(12) United States Patent
Kim et al.

(10) Patent No.: US 10,086,077 B2
(45) Date of Patent: Oct. 2, 2018

(54) ACTIVATED MACROPHAGE TARGETABLE DRUG CARRIER FOR TREATMENT OF ATHEROSCLEROSIS AND METHODS OF PREPARING THE SAME

(71) Applicants: Korea University Research and Business Foundation, Seoul (KR); IUCF-HYU (Industry-University Cooperation Foundation Hanyang University), Seoul (KR); Chung-Ang University Industry-Academy Cooperation Foundation, Seoul (KR)

(72) Inventors: Jin Won Kim, Seoul (KR); Hong Ki Yoo, Seoul (KR); Kyeong Soon Park, Gangwon-do (KR)

(73) Assignees: Korea University Research and Business Foundation, Seoul (KR); IUCF-HYU (Industry-University Cooperation Foundation Hanyang University), Seoul (KR); Chung-Ang University Industry-Academy Cooperation Foundation, Seoul (KR)

( * ) Notice: Subject to any disclaimer, the term of this patent is extended or adjusted under 35 U.S.C. 154(b) by 0 days.

(21) Appl. No.: 15/346,516

(22) Filed: Nov. 8, 2016

(65) Prior Publication Data

US 2017/0319699 A1 Nov. 9, 2017

(30) Foreign Application Priority Data

May 3, 2016 (KR) .................. 10-2016-0054752

(51) Int. Cl.
| | | |
|---|---|---|
| A61K 47/34 | (2017.01) | |
| A61K 9/51 | (2006.01) | |
| A61K 31/505 | (2006.01) | |
| A61K 47/28 | (2006.01) | |
| A61K 31/40 | (2006.01) | |
| A61K 31/506 | (2006.01) | |

(52) U.S. Cl.
CPC .............. *A61K 47/34* (2013.01); *A61K 9/513* (2013.01); *A61K 9/5123* (2013.01); *A61K 9/5161* (2013.01); *A61K 9/5192* (2013.01); *A61K 31/40* (2013.01); *A61K 31/505* (2013.01); *A61K 31/506* (2013.01); *A61K 47/28* (2013.01)

(58) Field of Classification Search
None
See application file for complete search history.

(56) References Cited

FOREIGN PATENT DOCUMENTS

| KR | 2010-0035062 A | 4/2010 |
|---|---|---|
| KR | 10-1142152 B1 | 5/2012 |

OTHER PUBLICATIONS

Kim et al., Clinical Therapeutics, 33(11), pp. 1819-1829. (Year: 2011).*
Alonso-Sande et al., Biomacromolecules, 14, pp. 4046-4052. (Year: 2013).*
Rigau et al., Nanoscale, 5, pp. 89-109. (Year: 2013).*
Wang et al., AAPS PharmSciTech, 14(2), pp. 585-592. (Year: 2013).*
Park et al., Tissue Engineering and Regenerative Medicine, 6(4-11), pp. 588-594. (Year: 2009).*
Lee et al. "Hyaluronic acid nanoparticles for active targeting atherosclerosis" Biomaterials 53 (2015) 341-348.
Chaubey et al. "Mannose-conjugated chitosan nanoparticles loaded with rifampicin for the treatment of visceral leishmaniasis" Carbohydrate Polymers 101 (2014) 1101-1108.
Choi et al. "Abstract 17815: The Effects of Nanoparticle-mediated PPARy Agonist Delivery on Plaque Stabilization: A Multichannel High-resolution Intravital Imaging Analysis" Thrombosis, Immunity and Inflammation, Session Title: Mechanisms of Cardiovascular Inflammation, Circulation. 2015; 132: A17815, pp. 1-2.

* cited by examiner

*Primary Examiner* — Abigail Vanhorn
(74) *Attorney, Agent, or Firm* — Casimir Jones, S.C.

(57) ABSTRACT

Provided is a drug carrier for treatment of atherosclerosis including a biocompatible amphipathic polymer including a macrophage ligand polymer and a hydrophobic substance, and a hydrophobic drug.

7 Claims, 26 Drawing Sheets

ACTIVATED MACROPHAGE TARGETABLE DRUG CARRIER FOR TREATMENT OF ATHEROSCLEROSIS AND METHODS OF PREPARING THE SAME

CROSS-REFERENCE TO RELATED APPLICATION(S)

This application claims the priority benefit of Korean Patent Application No. 10-2016-0054752 filed on May 3, 2016, in the Korean Intellectual Property Office, the disclosure of which is incorporated herein by reference for all purposes.

BACKGROUND

1. Field

One or more example embodiments relate to a drug carrier including a hydrophobic drug capable of recognizing activated macrophages present in atherosclerotic plaques.

2. Description of Related Art

Atherosclerosis is a disease in which harmful substances such as cholesterol are deposited on the inner wall of the blood vessel, the diameter of the blood vessel becomes narrow or clogged (stenosis) while proliferation of endothelial cells occurs, and the blood vessel causes a blood flow disorder to the end. The atherosclerosis is mainly shown in the coronary artery supplying blood to the heart, the cerebral artery and the carotid artery supplying the blood to the brain, the renal artery of the kidney, the peripheral blood vessel, and the like. The atherosclerosis is a chronic disease which is very slowly progressing and a very scared disease due to no symptom before appearing as the disease. Particularly, in the case of the coronary artery, there is no symptom or ambiguous at rest until the coronary artery narrows to 70% and thus diagnosis and treatment of angina are delayed in some cases. In development and progression of the atherosclerosis, simply, chronic Inflammation reaction as well as cholesterol metabolic disorder has a large effect. When atherosclerotic plaques with progressing inflammation is ruptured, complications including coronary artery diseases such as angina and myocardial infarction, stroke such as cerebral infarction and cerebral hemorrhage, renal failure and ischemic acropathy in which the kidney function is deteriorated, and the like are involved.

A low density lipoprotein (LDL) in the blood is accumulated in the extracellular matrix in a subcutaneous tissue over a threshold value in a combination of various risk factors and the accumulated LDL is oxidized with the hardness by an oxidized material in the tissue (minimally oxidized LDL). The minimally oxidized LDL acts in the endothelial cell and is attached to monocytes in the blood to increase expression of attachment materials VCAM-1, ICAM-1, and E-selectin required to move to the subcutaneous tissue and thus the monocytes are introduced. The introduced monocytes are differentiated to macrophages and promotes introduction of the monocytes by stimuli of oxidized LDL while being activated, and cell proliferating agents M-CSF, G/M-CSF, and PDGF, cytokines IL-1 and TNF-α involved in inflammation, and tissue factors promoting clotting are secreted, and the oxidized material is secreted, and thus the lipid is further oxidized to produce the oxidized LDL, and the oxidized LDL is ingested in large quantities through a scavenger receptor to be differentiated to foam cells with the deposited lipid. As described above, the activated macrophage is a cell which plays an important role in formation and progression of the atherosclerotic plaque. Particularly, when the lipid deposition by the activated macrophage is in progress in the atherosclerotic plaque, the atherosclerotic plaque is differentiated to the foam cell, and it is known that as the number is gradually increased, there is a close relation with rupture of the atherosclerotic plaque. Accordingly, with development of treating techniques in which the macrophage in the atherosclerotic plaque takes a large amount of oxidized lipid to suppress the macrophage from being differentiated to the foam cell or identify an inflammation inhibition mechanism in macrophages and suppress an inflammation occurrence mechanism, a possibility of decreasing occurrence of the atherosclerotic plaque and occurrence of complications thereof is very large.

Currently, treatment of the atherosclerosis has focused on prevention and inhibition of atherosclerosis by lowering the blood cholesterol concentration and treatment of stabilizing or reducing the pre-occurring atherosclerosis has not been performed so far. Drugs known to have anti-inflammatory and anti-lipid effects also require hundreds or dozens times larger than a human acceptable capacity for the effects and are difficult to be actually applied to the clinical trials.

In order to overcome the problems, recently, study results in which a drug called pitavastatin is biocompatible and physically encapsulated in a nanoparticle constituted by poly(lactic-co-glycolic acid) as a biodegradable polymer to prepare a nano medicine and in an atherosclerotic mouse model, destabilization and rupture of the atherosclerotic plaque are decreased by using the nano medicine have been reported (Katsuki et al, Circulation, 2014, 129, 896-906). However, in the literature, it is considered that an effect of reducing the destabilization and rupture of the atherosclerotic plaque is not large and this is a method of treating arteriosclerosis depending on phagocytosis of monocytes or macrophages of nanoparticles, and further, efficiency of delivering selectively the drug to the disease portion is low. Accordingly, the inventors developed a drug carrier capable of maximizing a treating effect by target-delivering the drug to the atherosclerotic plaque more selectively at a high concentrate, by impregnating an atherosclerotic plaque stabilizing or treating drug in the nanoparticles which can be selectively targeted to the activated macrophage of the atherosclerotic plaque and selectively accumulated in the tissue of the atherosclerotic plaque.

SUMMARY

An aspect provides a drug carrier for treatment of atherosclerosis including a first amphipathic polymer including a macrophage ligand polymer and a hydrophobic substance, and a hydrophobic drug.

Another aspect provides a drug carrier for treatment of atherosclerosis including a second amphipathic polymer including a hydrophilic polymer, a hydrophobic substance, and a target ligand recognizing the macrophage, and a hydrophobic drug.

Still another aspect provides a drug carrier for treatment of atherosclerosis including two types or more amphipathic polymers, and a hydrophobic drug.

The drug carrier is selectively target-bound to receptors expressed in the activated macrophages in atherosclerotic plaques to deliver a drug at a high concentration, thereby suppressing the spread of atherosclerotic diseases at all stages of development, progression and rupture of atherosclerosis and preventing various complications due to atherosclerosis.

However, aspects to be achieved are not limited to the aforementioned aspects, and other not-mentioned aspects will be obviously understood by those skilled in the art from the description below.

According to a first aspect, there is provided a drug carrier for treatment of atherosclerosis including a first amphipathic polymer including a macrophage ligand polymer and a hydrophobic substance, and a hydrophobic drug.

The first amphipathic polymer may further include a target ligand that recognizes macrophages.

According to a second aspect, there is provided a drug carrier for treatment of atherosclerosis including a second amphipathic polymer including a hydrophilic polymer, a hydrophobic substance, and a target ligand recognizing the macrophage, and a hydrophobic drug.

The drug carrier may further include a hydrophobic synthetic polymer.

The hydrophobic synthetic polymer may include at least one of poly(caprolactone), poly(lactic acid), poly(glycolic acid), poly(lactic-co-glycolic acid), poly(styrene), poly(lactic-co-caprolactone), poly(divinyl ether-co-maleic anhydride), poly(styrene-co-maleic anhydride), derivatives of these polymers, and pegylated derivatives of these polymers.

According to a third aspect, there is provided a drug carrier for treatment of atherosclerosis including a first amphipathic polymer including a macrophage ligand polymer and a hydrophobic substance, a second amphipathic polymer including a hydrophilic polymer, a hydrophobic substance, and a target ligand recognizing the macrophage, and a hydrophobic drug.

The drug carrier may further include a hydrophobic synthetic polymer.

According to a fourth aspect, there is provided a drug carrier for treatment of atherosclerosis including a third amphipathic polymer including a macrophage ligand polymer, a hydrophobic substance, and a target ligand recognizing the macrophage, a second amphipathic polymer including a hydrophilic polymer, a hydrophobic substance, and a target ligand recognizing the macrophage, and a hydrophobic drug.

The drug carrier may further include a hydrophobic synthetic polymer.

The hydrophobic synthetic polymer may include at least one of poly(caprolactone), poly(lactic acid), poly(glycolic acid), poly(lactic-co-glycolic acid), poly(styrene), poly(lactic-co-caprolactone), poly(divinyl ether-co-maleic anhydride), poly(styrene-co-maleic anhydride), derivatives of these polymers, and pegylated derivatives of these polymers.

The macrophage ligand polymer may include a scavenger receptor or a hyaluronan receptor (CD44).

The ligand polymer of the scavenger receptor may be a dextran derivative polymer or a fucoidan derivative polymer, or the ligand polymer of the hyaluronan receptor may be a hyaluronic acid derivative polymer.

The hydrophilic polymer may include at least one of a dextran derivative, a fucoidan derivative, a hyaluronic acid derivative, a chitosan derivative, poly-L-lysine, poly-aspartic acid, poly(divinyl ether-co-maleic anhydride), poly(styrene-co-maleic anhydride), poly-lactic acid, poly(lactic-co-glycolic acid), and derivatives thereof.

The hydrophobic substance may include at least one of bile acid derivatives, stearic acid, palmitic acid, oleic acid, and cholesterol derivatives.

The target ligand recognizing the macrophage may include at least one of mannose amine and mannose phosphate capable of recognizing mannose receptors of macrophages; CRKRLDRNC peptide and derivatives thereof capable of recognizing IL-4 receptors of the macrophages; folic acid and derivatives thereof capable of recognizing folate receptors of the macrophages; peptides for CD36, CD44, CD80, and CD86 receptors of macrophages and derivatives thereof; and peptides for CXCR1, CXCR2, and CXCR6 receptors of macrophages and derivatives thereof.

The hydrophobic drug may include at least one of statin drugs, PPAR-gamma agonist drugs, DPP-4 inhibitor drugs, angiotensin converting enzyme inhibitor drugs, angiotensin II receptor blockers, PCSK9 inhibitors, and antioxidants.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the disclosure will become apparent and more readily appreciated from the following description of example embodiments, taken in conjunction with the accompanying drawings of which.

DETAILED DESCRIPTION

Figure 1:
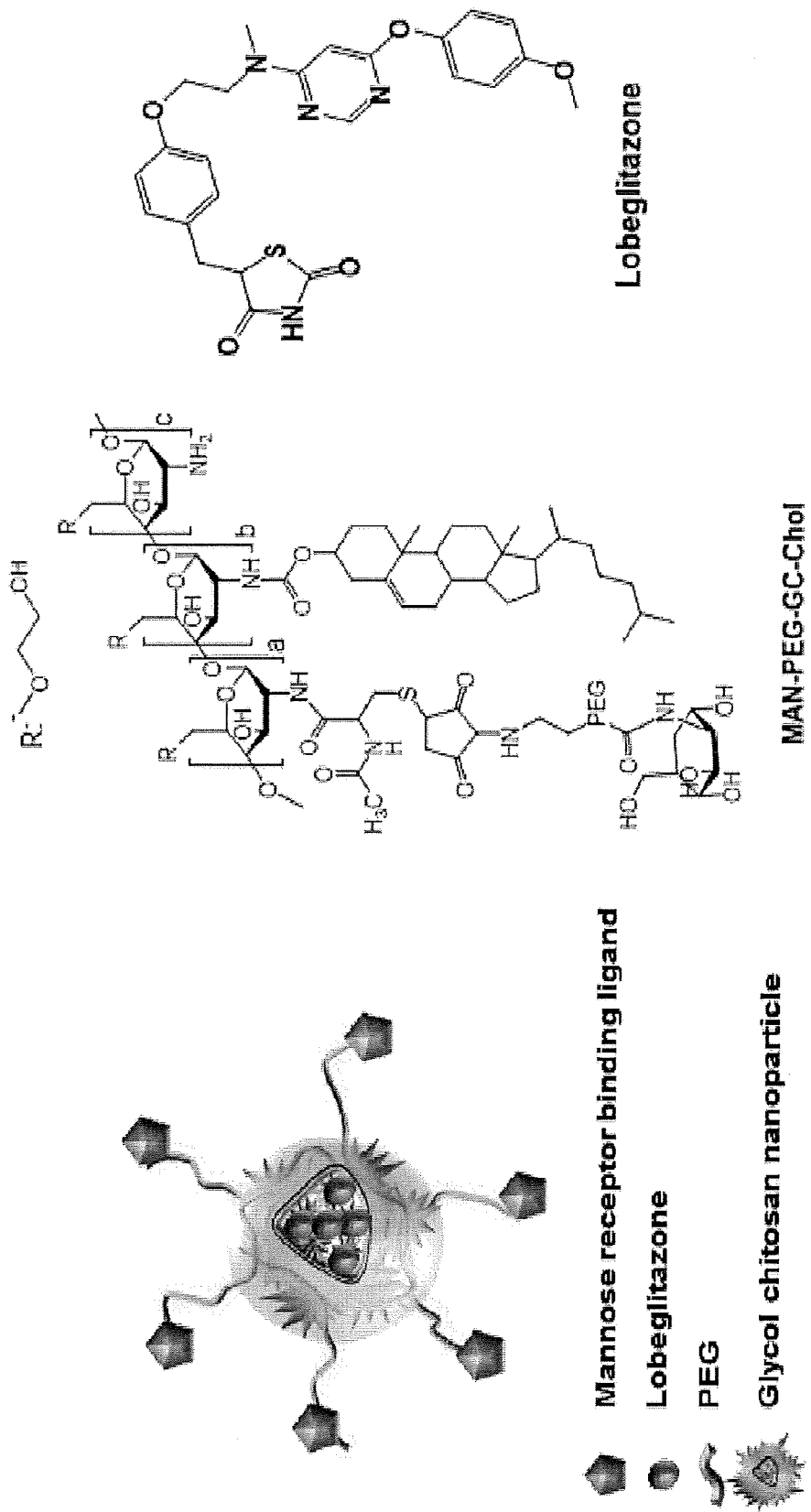
FIG. 1 is Chemical Formula of an amphipathic polymer in which a hydrophobic substance and a macrophage target ligand are bound to a biopolymer and a drug.

Hereinafter, an example embodiment will be described in more detail with reference to the accompanying drawings. Like reference numerals illustrated in the respective drawings designate like members.

Various modifications may be applied to example embodiments to be described below. The example embodiments to be described below are not limited to aspects and need to be understood by including all modifications, equivalents, and substitutions.

Terms used in the example embodiments are used only to describe specific example embodiments, and are not intended to limit the example embodiments. Singular expressions used herein include plurals expressions unless they have definitely opposite meanings. In this specification, it should be understood that term "include" or "have" indicates that a feature, a number, a step, an operation, a component, a part or the combination thereof described in the specification is present, but does not exclude a possibility of presence or addition of one or more other features, numbers, steps, operations, components, parts or combinations, in advance.

If it is not contrarily defined, all terms used herein including technological or scientific terms have the same meaning as those generally understood by a person with ordinary skill in the art. Terms defined in generally used dictionary shall be construed that they have meanings matching those in the context of a related art, and shall not be construed in ideal or excessively formal meanings unless they are clearly defined in the present application.

Further, example embodiments will be described in detail with reference to the accompanying drawings, in which like reference numerals refer to like or similar elements regardless of reference numerals and a duplicated description thereof will be omitted. In describing the example embodiments, when it is determined that the detailed description of the publicly known art related to the present disclosure may obscure the gist of the example embodiments, the detailed description thereof will be omitted.

One or more example embodiments relate to a drug carrier including a biocompatible polymer; and a hydrophobic drug. The biocompatible polymer usable is a polymer having excellent stability in vivo and also includes a synthetic polymer as well as a ligand polymer and a natural polymer which are selectively bound to receptors of activated macrophages. According to an example embodiment, the biocompatible natural polymer may use dextran derivative polymers (dextran, dextransulfate, and carboxymethyl dextran) as the ligand polymer of the macrophage receptor and fucoidan derivative polymers (fucoidan and fucoidan sulfate), which are ligand polymers and may use hyaluronic acid polymers as ligand polymers of hyaluronan receptors (CD44) and derivatives thereof, and chitosan derivative polymers (chitosan, methylglycol chitosan, chitosan oligosaccharide, Glycol chitosan), and the like. Further, the synthetic polymer may use poly-L-lysine, poly-aspartic acid, poly(divinyl ether-co-maleic anhydride), poly(styrene-co-maleic anhydride), poly-lactic acid, poly(lactic-co-glycolic acid), derivatives thereof, and the like. The polymer nanoparticles need to have biocompatibility/biodegradability in vivo and has excellent stability in vivo to require a characteristic in which the polymer nanoparticles are continuously accumulated in an atherosclerotic plaque tissue while being circulated for a sufficient time in the blood.

Figure 14:
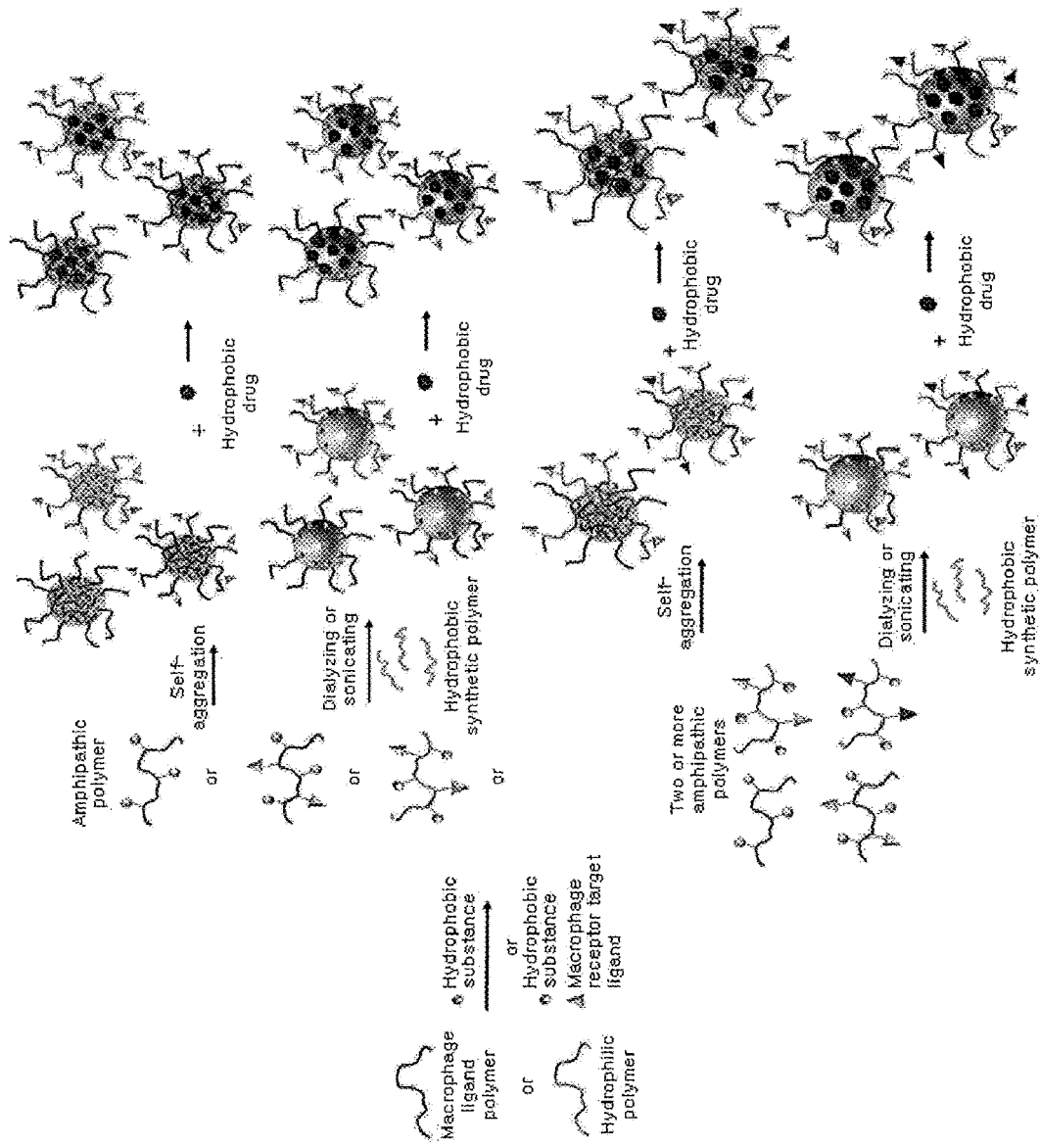
FIG. 14 illustrates an overall reaction schematic diagram of the drug carrier according to an example embodiment.

FIG. 14 illustrates an overall reaction schematic diagram of the drug carrier. Hereinafter, the reaction schematic diagram of FIG. 14 will be described by divided parts.

Figure 15:
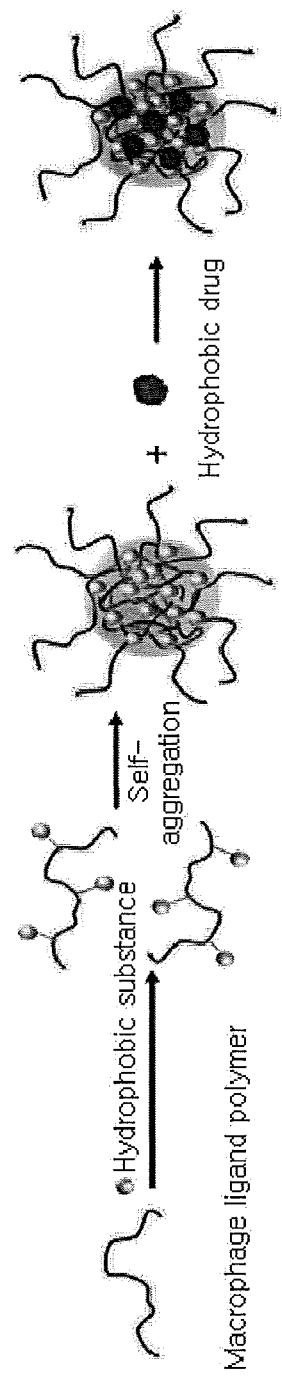
FIG. 15 is a Reaction schematic diagram 1 illustrating an example embodiment.

FIG. 15 is a Reaction schematic diagram 1 illustrating an example embodiment.

A first aspect provides a drug carrier for treatment of atherosclerosis including a first amphipathic polymer including a macrophage ligand polymer and a hydrophobic substance, and a hydrophobic drug.

The term "macrophage ligand polymer" used is biocompatible and called a ligand polymer which can be selectively bound to the receptor of the activated macrophage. The macrophage ligand polymer includes dextran derivative polymers (dextran, dextransulfate, and carboxymethyl dextran) as a ligand polymer of a scavenger receptor, fucoidan derivative polymers (fucoidan and fucoidan sulfate), and hyaluronic acid polymers as ligand polymers of hyaluronan receptors (CD44) and derivatives thereof.

According to an example embodiment, the macrophage ligand polymer may be at least one of dextran, dextransulfate, and carboxymethyl dextran. Particularly, the dextransulfate is known as the ligand polymer of the scavenger receptor in which the activated macrophages are overexpressed and selectively bound to the ligand polymer of the scavenger receptor to have high absorbed cumulative efficiency, and a hydroxyl group (OH) of the dextransulfate may induce chemical reformation using the hydrophobic substance.

According to an example embodiment, the hydrophobic substance may be at least one of bile acid derivatives (deoxycholic acid, lithocholic acid, taurodeoxycholic acid, and glycochenodeoxycholic acid), stearic acid, palmitic acid, olelic acid, and cholesterol derivatives (cholesterol, cholesteryl ester, cholesteryl chloroformate, and cholesteryl benzoate). According to an example embodiment, the cholesterol derivatives may be at least one of cholesteryl ester, cholesteryl chloroformate, and cholesteryl benzoate and more preferably, cholesteryl chloroformate.

The first amphipathic polymer including the macrophage ligand polymer and the hydrophobic substance may form nanoparticles which can be self-assembled by a hydrophobic and hydrophilic balance. The nanoparticles may selectively deliver and accumulate the drug to the atherosclerotic plaques by recognizing the macrophage through the macrophage ligand polymer after impregnating the hydrophobic drug.

Figure 16:
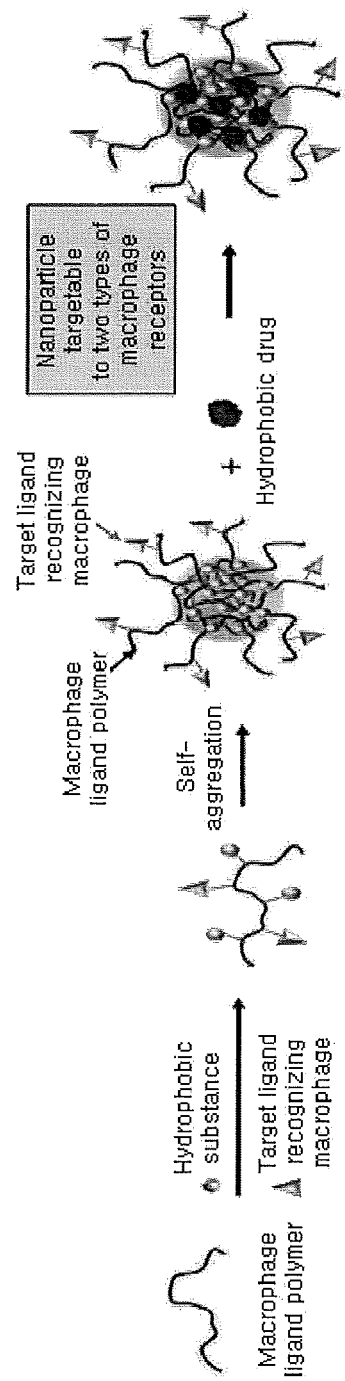
FIG. 16 is a Reaction schematic diagram 2 illustrating an example embodiment.

FIG. 16 is a Reaction schematic diagram 2 illustrating an example embodiment.

According to an example embodiment, the amphipathic polymer including the macrophage ligand polymer and the hydrophobic substance may further include a target ligand recognizing the macrophage. In this specification, this is called a 'third amphipathic polymer'. The third amphipathic polymer includes the macrophage ligand polymer and the target ligand recognizing the macrophage to configure nanoparticles recognizing two receptors of the macrophage once.

The target ligand recognizing the macrophage may be a ligand, peptide, or antibody for the receptor expressed in the activated macrophage in the atherosclerotic plaque. More particularly, the target ligand recognizing the macrophage may include at least one of mannose amine and mannose phosphate capable of recognizing mannose receptors of macrophages; CRKRLDRNC peptide and derivatives thereof capable of recognizing IL-4 receptors of the macrophages; folic acid and derivatives thereof capable of recognizing folate receptors of the macrophages; peptides for CD36, CD44, CD80, and CD86 receptors of macrophages and derivatives thereof; and peptides for CXCR1, CXCR2, and CXCR6 receptors of macrophages and derivatives thereof.

Figure 17:
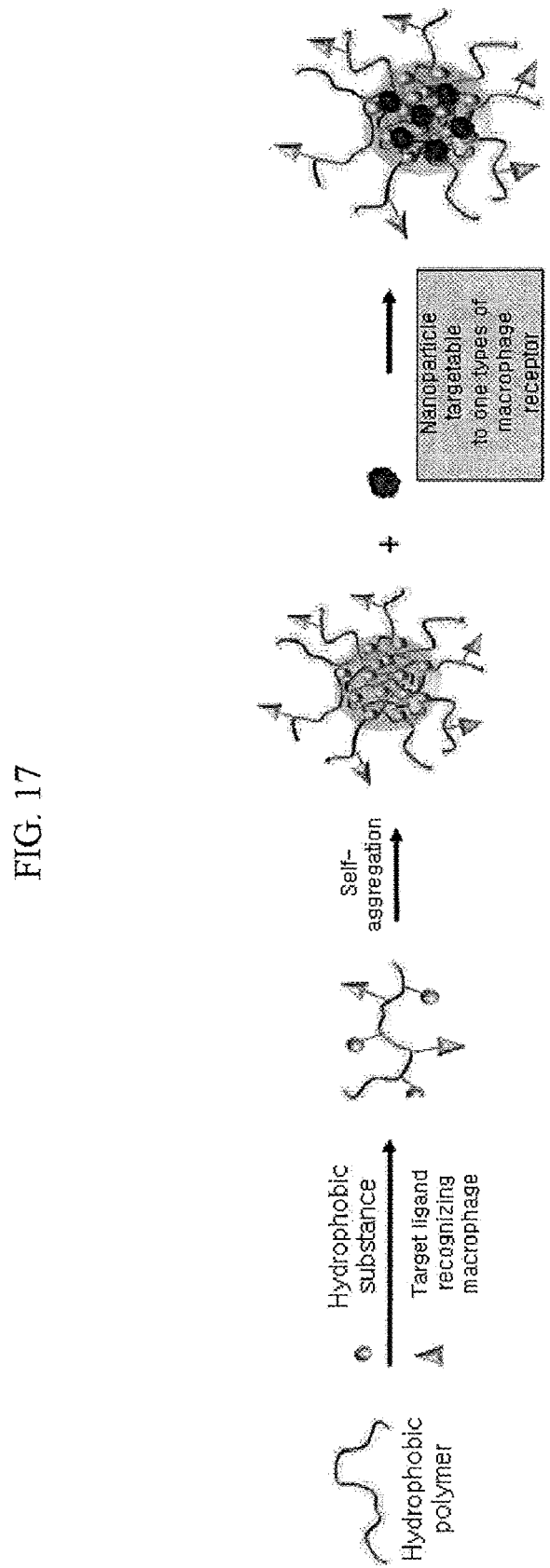
FIG. 17 is a Reaction schematic diagram 3 illustrating an example embodiment.

FIG. 17 is a Reaction schematic diagram 3 illustrating an example embodiment.

A second aspect also provides a drug carrier for treatment of atherosclerosis including a second amphipathic polymer including a hydrophilic polymer, a hydrophobic substance, and a target ligand recognizing the macrophage, and a hydrophobic drug.

According to an example embodiment, the hydrophilic polymer may include at least one of a dextran derivative, a fucoidan derivative, a hyaluronic acid derivative, a chitosan derivative, poly-L-lysine, poly-aspartic acid, poly(divinyl ether-co-maleic anhydride), poly(styrene-co-maleic anhydride), poly-lactic acid, poly(lactic-co-glycolic acid), and derivatives thereof.

According to an example embodiment, the hydrophilic chitosan derivative which may be used may be at least one of chitosan, methyl glycol chitosan, chitosan oligosaccharide and glycol chitosan. Particularly, the glycol chitosan includes a lot of positrons in a polymer chain to have high cumulative efficiency absorbed in the tissue and an amine group of the glycol chitosan may induce chemical reformation using the hydrophobic substance.

The second amphipathic polymer including the hydrophilic polymer, the hydrophobic substance, and the target ligand recognizing the macrophage may form nanoparticles which can be self-assembled by the hydrophobic and hydrophilic balance. The nanoparticles may selectively deliver and accumulate the drug to the atherosclerotic plaques by recognizing the macrophage through the target ligand recognizing the macrophage after impregnating the hydrophobic drug.

According to an example embodiment, the hydrophobic substance may be at least one of bile acid derivatives (deoxycholic acid, lithocholic acid, taurodeoxycholic acid, and glycochenodeoxycholic acid), stearic acid, palmitic acid, olelic acid, and cholesterol derivatives (cholesterol, cholesteryl ester, cholesteryl chloroformate, and cholesteryl benzoate). According to an example embodiment, the cholesterol derivatives may be at least one of cholesteryl ester, cholesteryl chloroformate, and cholesteryl benzoate and more preferably, cholesteryl chloroformate.

The target ligand recognizing the macrophage may be a ligand, peptide, or antibody for the receptor expressed in the activated macrophage in the atherosclerotic plaque. More particularly, the target ligand recognizing the macrophage may include at least one of mannose amine and mannose phosphate capable of recognizing mannose receptors of macrophages; CRKRLDRNC peptide and derivatives thereof capable of recognizing IL-4 receptors of the macrophages; folic acid and derivatives thereof capable of recognizing folate receptors of the macrophages; peptides for CD36, CD44, CD80, and CD86 receptors of macrophages and derivatives thereof; and peptides for CXCR1, CXCR2, and CXCR6 receptors of macrophages and derivatives thereof.

Figure 18:
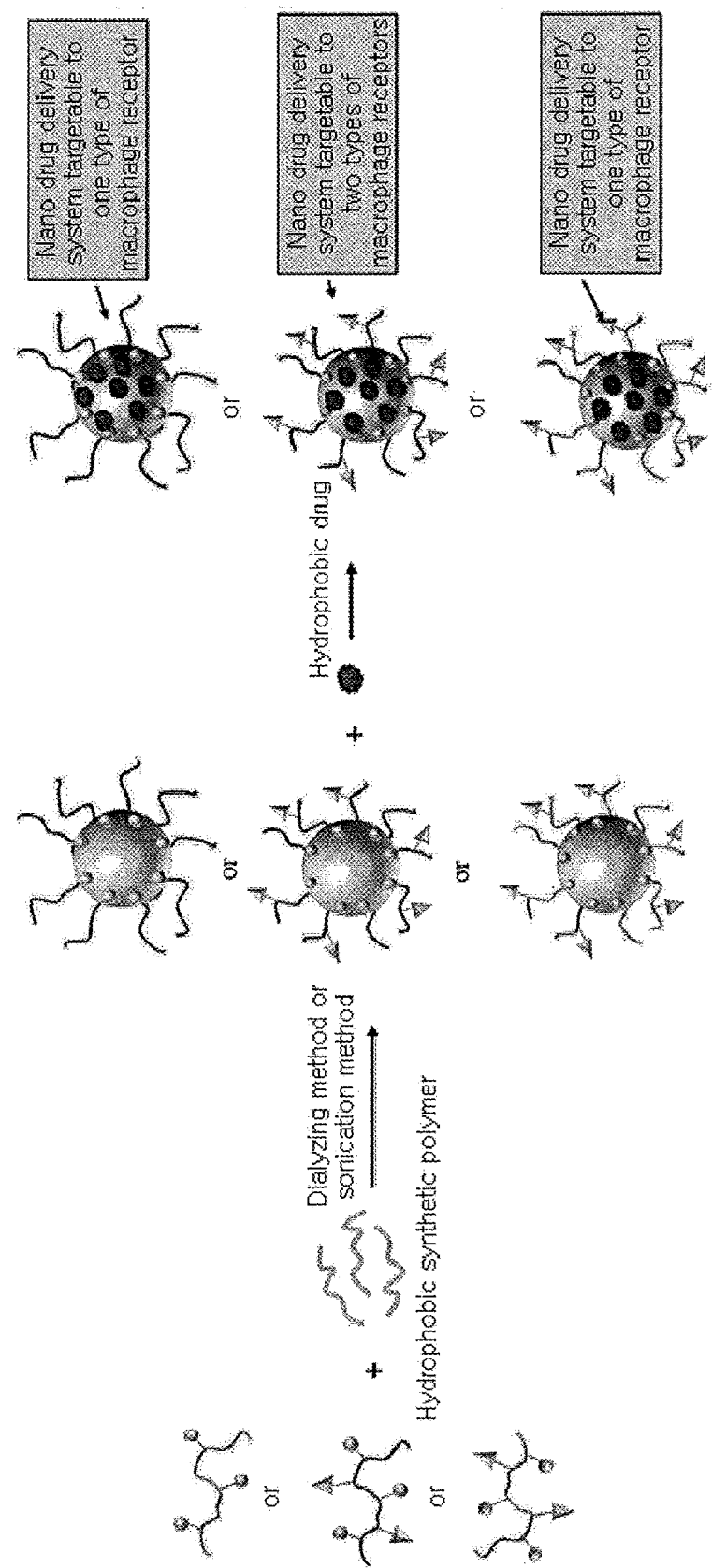
FIG. 18 is a Reaction schematic diagram 4 illustrating an example embodiment.

FIG. 18 is a Reaction schematic diagram 4 illustrating an example embodiment.

Each of the drug carrier including the first amphipathic polymer including the macrophage ligand polymer and the hydrophobic substance; the drug carrier including the third amphipathic polymer including the macrophage ligand polymer, the hydrophobic substance, and the target ligand recognizing the macrophage; or the drug carrier including the second amphipathic polymer including the hydrophilic polymer, the hydrophobic substance, and the target ligand recognizing the macrophage, described in the first and second aspects, may further include a hydrophobic synthetic polymer.

The hydrophobic synthetic polymer may include at least one of poly(caprolactone), poly(lactic acid), poly(glycolic acid), poly(lactic-co-glycolic acid), poly(styrene), poly(lactic-co-caprolactone), poly(divinyl ether-co-maleic anhydride), poly(styrene-co-maleic anhydride), derivatives of these polymers, and pegylated derivatives of these polymers.

When the amphipathic polymer and the hydrophobic synthetic polymer are mixed with each other, a different type of nanoparticles may be formed through the hydrophobic and hydrophilic balance.

Figure 19:
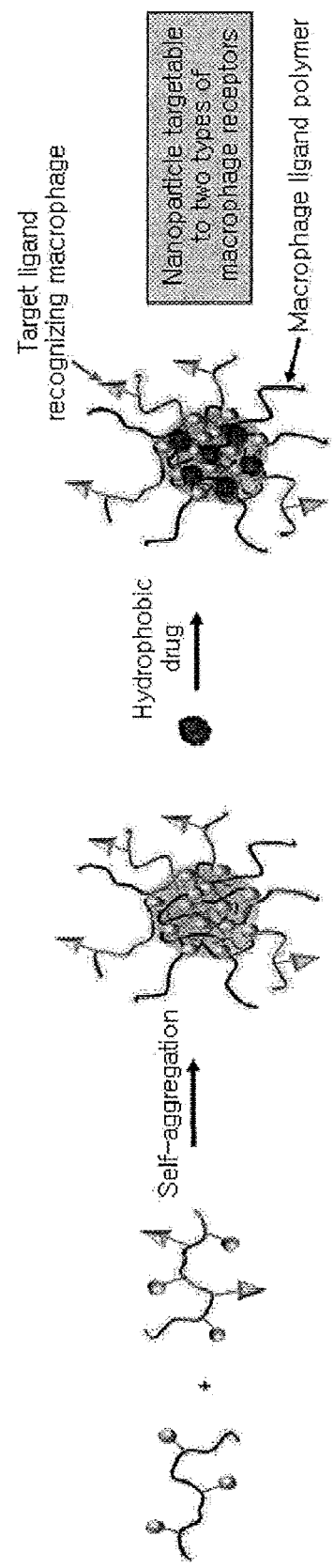
FIG. 19 is a Reaction schematic diagram 5 illustrating an example embodiment.

FIG. 19 is a Reaction schematic diagram 5 illustrating an example embodiment.

A third aspect provides a drug carrier for treatment of atherosclerosis including a first amphipathic polymer including a macrophage ligand polymer and a hydrophobic substance, a second amphipathic polymer including a hydrophilic polymer, a hydrophobic substance, and a target ligand recognizing the macrophage, and a hydrophobic drug.

The macrophage ligand polymer, the hydrophobic substance, the hydrophilic polymer, and the target ligand recognizing the macrophage configuring the drug carrier will be described in more detail with reference to the aforementioned parts.

Figure 20:
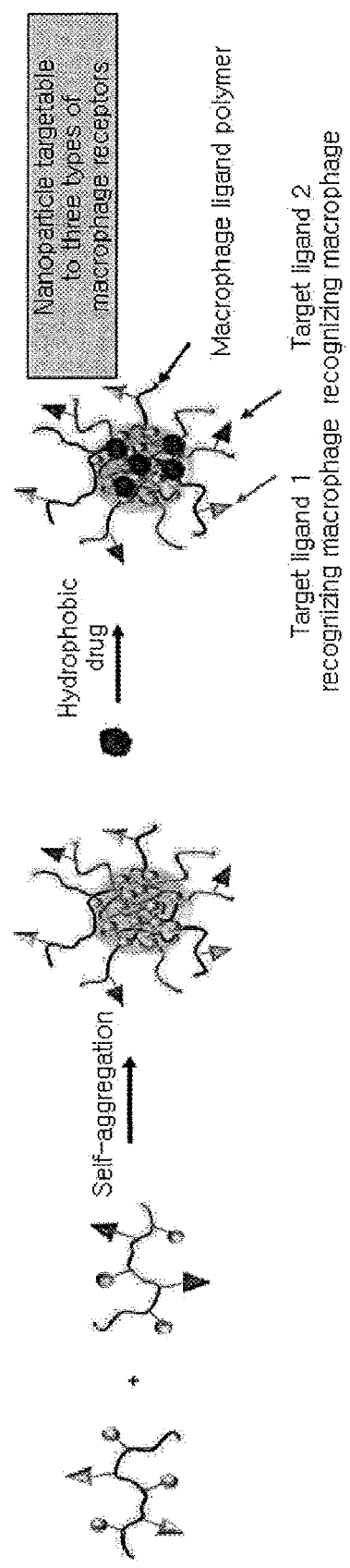
FIG. 20 is a Reaction schematic diagram 6 illustrating an example embodiment.

FIG. 20 is a Reaction schematic diagram 6 illustrating an example embodiment.

A fourth aspect provides a drug carrier for treatment of atherosclerosis including a third amphipathic polymer including a macrophage ligand polymer, a hydrophobic substance, and a target ligand recognizing the macrophage, a second amphipathic polymer including a hydrophilic polymer, a hydrophobic substance, and a target ligand recognizing the macrophage, and a hydrophobic drug.

The macrophage ligand polymer, the hydrophobic substance, the hydrophilic polymer, and the target ligand recognizing the macrophage configuring the drug carrier will be described in more detail with reference to the aforementioned parts.

Figure 21:
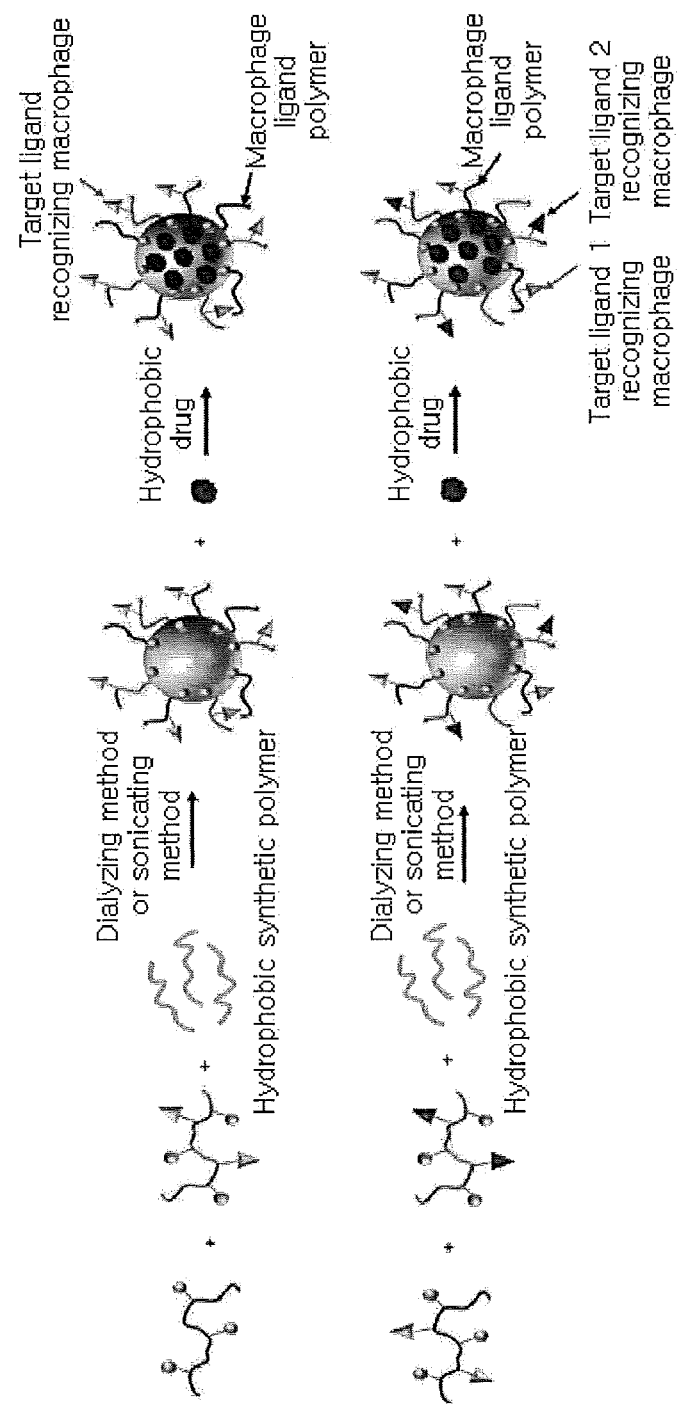
FIG. 21 is a Reaction schematic diagram 7 illustrating an example embodiment.

FIG. 21 is a Reaction schematic diagram 7 illustrating an example embodiment.

The drug carrier described in the third aspect or the fourth aspect may further include a hydrophobic synthetic polymer.

The hydrophobic synthetic polymer may include at least one of poly(caprolactone), poly(lactic acid), poly(glycolic acid), poly(lactic-co-glycolic acid), poly(styrene), poly(lactic-co-caprolactone), poly(divinyl ether-co-maleic anhydride), poly(styrene-co-maleic anhydride), derivatives of these polymers, and pegylated derivatives of these polymers.

As described in the third aspect or the fourth aspect, when the nanoparticles including different types of amphipathic polymers further include the hydrophobic synthetic polymer, various types of nanoparticles may be formed by the hydrophobic and hydrophilic balance.

The drug carrier has a nanoparticle form in which the surface is hydrophilic and the inside is hydrophobic due to the amphipathic polymer. Further, the drug carrier including the amphipathic polymer and the hydrophobic synthetic polymer has a nanoparticle form in which hydrophilic polymer is disposed on the surface and the hydrophobic substance and the hydrophobic synthetic polymer are disposed at the inside. The drug carrier may impregnate the hydrophobic drug due to the inner hydrophobic part.

FIG. 1 is Chemical Formulas of an amphipathic polymer and a hydrophobic drug, and a schematic diagram of a drug carrier according to an example embodiment.

More particularly, FIG. 1 illustrates a binding structure and a Chemical Formula of a drug carrier (MMR-Lobe) to which a ligand which can selectively target a mannose receptor of an activated macrophage of an atherosclerotic plaque, glycol chitosan nanoparticles, and lobeglitazone as a hydrophobic drug are bound.

According to an aspect, the hydrophobic drug may include at least one of statin drugs, PPAR-gamma agonist drugs, DPP-4 inhibitor drugs, angiotensin converting enzyme inhibitor drugs, angiotensin II receptor blockers, PCSK9 inhibitors, and antioxidants. The drug which may be used is a hydrophobic substance and may include all drugs in which anti-inflammatory, anti-lipid, and antioxidant effects for stabilizing and treating atherosclerosis are known. For example, the hydrophobic drug may be at least one of statin drugs (Atorvastatin, Rosuvastatin, Pitavastatin, Simvastatin, Pravastatin, Fluvastatin, Lovastatin, and the like), PPAR-gamma agonist drugs Lobeglitazone, Rosiglitazone, Pioglitazone, and the like), DPP-4 inhibitor drugs (Sitagliptin, Saxagliptin, Vildagliptin, Linagliptin, Alogliptin), angiotensin converting enzyme inhibitor drugs (Benazepril, Captopril, Cilazapril, Enalapril, Fosipril, Imidapril, Lisinopril, Moexipril, Perindopril, Quinapril, Ramipril, Trandolapril), angiotensin II receptor blockers (Losartan, Candesartan, Valsartan, Irbesartan, Telmisartan, Eprosartan, Olmesartan, Azilsartan, Fimasartan), PCSK9 inhibitors (Evolocumab, Bococizumab, Alirocumab), and antioxidants (Ascorbate, Resveratrol, Curcumin, EGCG, MitoQ, N-acetylcysteine, EUK-8, NecroX, MnTBAP, and the like). The hydrophobic drug is encapsulated in the inside of the amphiphilic nanoparticle having hydrophobicity and delivered to the target cell to screen cells or tissues of the atherosclerotic disease or suppress the progression of the diseased in the steps of development, progression, rupture, and the like of the atherosclerosis, and may also be used to prevent various complications caused by the arteriosclerosis.

Further, the drug carrier which can selectively target the activated macrophage in the atherosclerotic plaque prepared has a stable nanoparticle structure in an aqueous system and the size of the drug carrier which can target the activated macrophage in the atherosclerotic plaque preferably has a size of 50 to 500 nm and is characterized by forming a sphere.

Further, the drug carrier which can selectively target the activated macrophage in the atherosclerotic plaque prepared has the stable nanoparticle structure in the aqueous system to encapsulate inorganic nanoparticles having hydrophobicity and a particle size of 1 to 20 nm or less, for example, gold nanoparticles, iron oxide nanoparticles, manganese oxide nanoparticles, quantum dots, hydrophobic phosphors, and the like. In addition, while the size of the atherosclerotic plaque and the inflammation change are monitored in real time by using these materials and optical imaging, CT, and MRI equipment in real time, therapeutic efficacy evaluation is possible.

According to an example embodiment, a method of preparing a drug carrier includes preparing an amphipathic polymer, forming nanoparticles by self-assembling the amphipathic polymer; and impregnating a hydrophobic drug in the nanoparticles.

According to an example embodiment, a method of preparing a drug carrier includes preparing an amphipathic polymer, forming nanoparticles by mixing a hydrophobic synthetic polymer with the amphipathic polymer and then sonicating or dialyzing the mixture; and impregnating a hydrophobic drug in the nanoparticles.

The amphipathic polymer may be at least one of the aforementioned first, second, and third amphipathic polymers. For example, a method of preparing the first amphipathic polymer includes chemically binding the hydrophobic substance to the macrophage ligand polymer by using a crosslinker. A method of preparing the second amphipathic polymer includes chemically binding the hydrophilic molecule, the hydrophobic substance, and the target ligand recognizing the macrophage by using a crosslinker. A method of preparing the third amphipathic polymer includes chemically binding the macrophage ligand polymer, the hydrophobic substance, and the target ligand recognizing the macrophage by using a crosslinker.

For the preparing of nanoparticles by the mixing of the hydrophobic synthetic polymer with the amphipathic polymer and then the sonicating or dialyzing of the mixture, a sonicating method capable of preparing the nanoparticles having a size of 100 to 500 nm is more preferable.

The macrophage ligand polymer, the hydrophobic substance, the hydrophilic polymer, and the target ligand recognizing the macrophage configuring the drug carrier will be described in more detail with reference to the aforementioned parts.

Example 1: Preparation of Activated Macrophage Targetable Nanoparticles Impregnated with Atherosclerosis Treating Agent 500 mg of glycol chitosan was dissolved in 100 ml of a 4-morpholineethane sulfonic acid (MES, pH 5.6) buffer, added with 16.3 mg of N-acetylcysteine, 28.7 mg of 1-ethyl-3-(3-dimethyl-aminopropyl) carbodiimide (EDC), and 17.3 mg of N-hydrosuccinimide (NHS), and then reacted for 48 hours. Thereafter, the reaction solution was dialyzed for 2 days to remove a non-reaction material and then lyophilized to prepare thiolated glycol chitosan.

400 mg of thiolated glycol chitosan prepared above was dissolved in 80 ml of a PBS (pH 6.9) buffer solution and reacted with 100 mg of mannose-Polyethylene glycol-maleimide (MAN-PEG-MAL) for 20 hours, and then the reaction solution was dialyzed for 2 days and lyophilized to prepare mannose-polyethylene glycol-glycol chitosan (MAN-PEG-GC).

Figure 22:
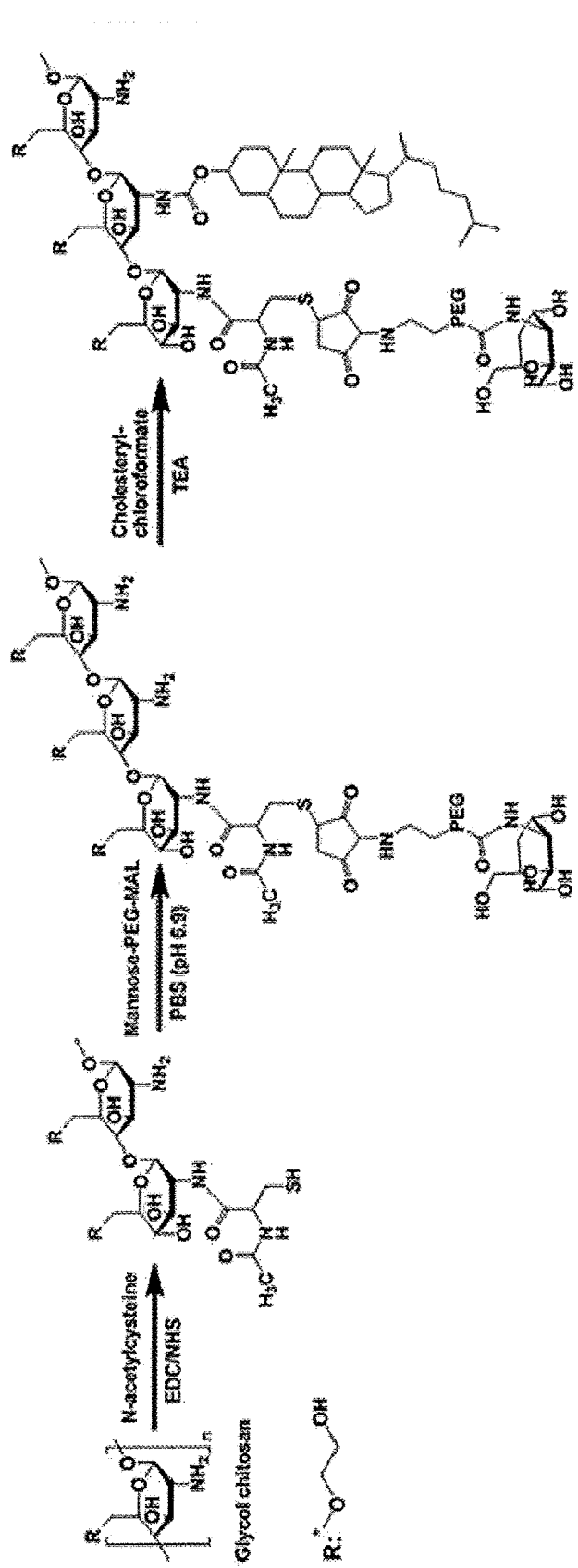
FIG. 22 illustrates a Reaction Formula 1.

100 mg of MAN-PEG-GC prepared above and 5 mg of cholesteryl chloroformate were dissolved in 20 ml of a dimethyl sulfoxide:dimethylformamide (3:1) co-solvent and added with 9 μl of triethyleneamine (TEA), and reacted for 24 hours. The reaction solution was dialyzed for 2 days and lyophilized to prepare nanoparticles MAN-PEG-GC-Chol which can target the activated macrophage of atherosclerosis. These prepared processes are shown in FIG. 22 illustrating a Reaction Formula 1.

100 mg of the MAN-PEG-GC-Chol obtained after lyophilizing and 30 mg of lobeglitazone were dissolved in dimethylsulfide and the mixture was dialyzed for 1 day and lyophilized to prepare an activated macrophage targetable drug carrier encapsulated with the lobeglitazone as the atherosclerotic treating agent.

Figure 23:
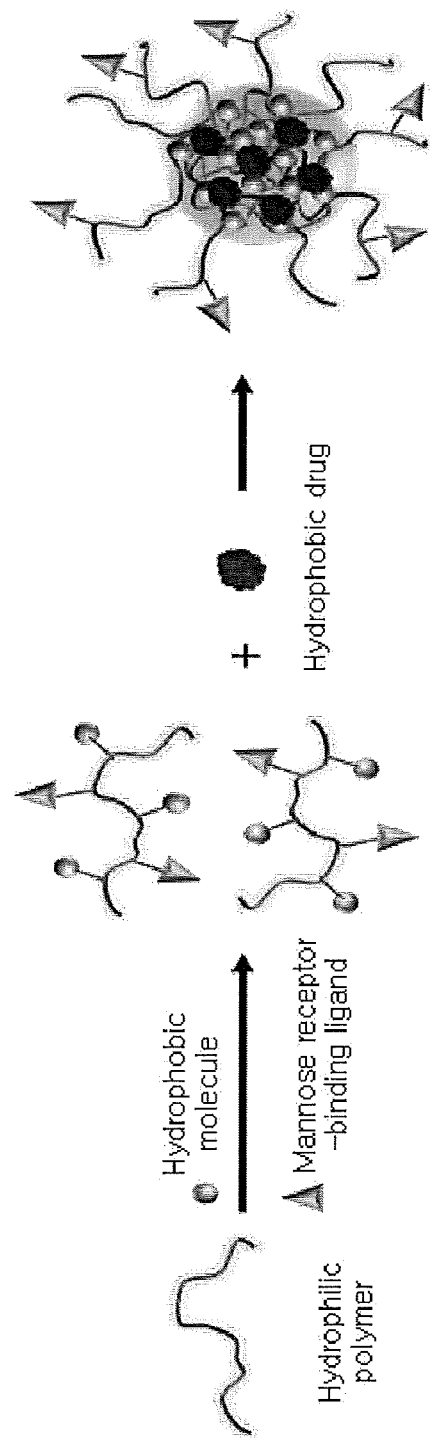
FIG. 23 illustrates a Reaction Formula 2.

The activated macrophage targetable drug carrier encapsulated with the lobeglitazone was prepared by impregnating the lobeglitazone in the nanoparticles of MAN-PEG-GC-Chol consisting of hydrophilic residues and hydrophobic residues by hydrophobic interaction and the preparing principle thereof is shown as FIG. 23 illustrating a Reaction Formula 2.

EXPERIMENTAL EXAMPLES

Experimental Example 1: Analysis of Particle Size and Drug Encapsulation Efficiency of Drug Carrier 1 mg of the activated macrophage targetable drug carrier encapsulated with the lobeglitazone obtained after lyophilizing was dissolved in a co-solvent of acetonitrile:water:formic acid (60:40:0.25, v/v/v), 5 μl of the drug carrier solution was taken and injected to a high performance liquid chromatography system, and 0.5 ml/min of the co-solvent of acetonitrile:water:formic acid (60:40:0.25, v/v/v) flowed to analyze drug encapsulation efficiency. Further, the particle size and shape after encapsulating the lobeglitazone were analyzed by a transmission electron microscopy after dispersing 1 mg of the drug carrier encapsulated with the lobeglitazone in distilled water.

Figure 2:
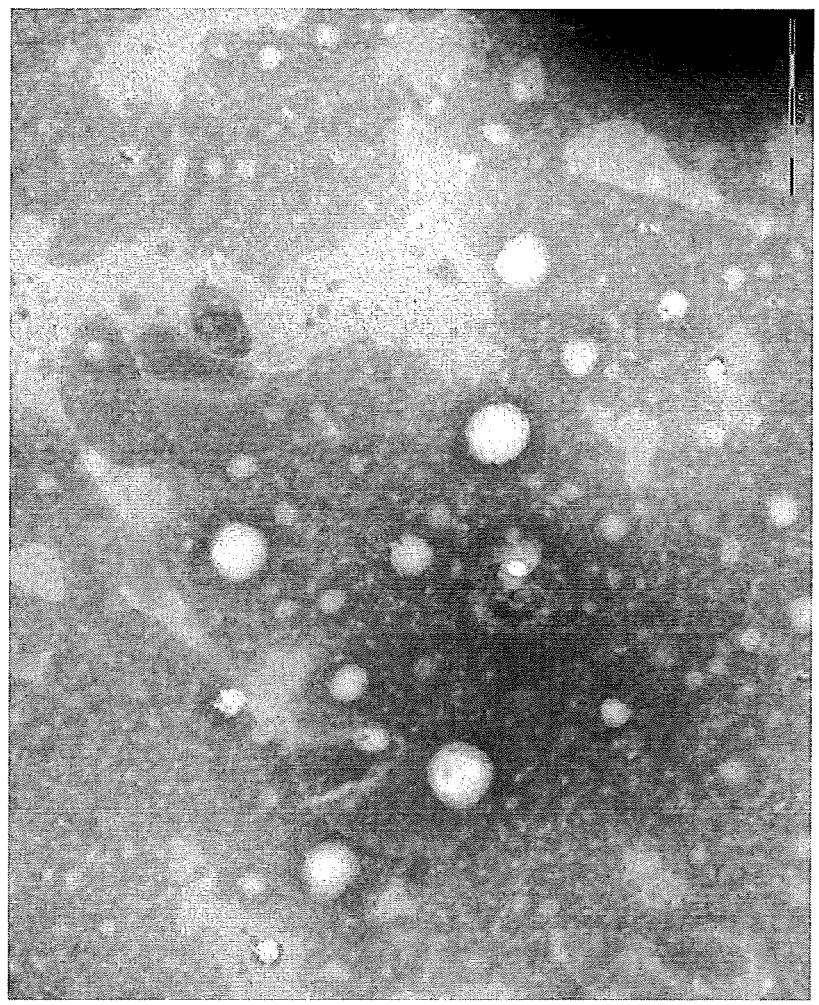
FIG. 2 is a transmission electron micrograph of a drug carrier in which the hydrophobic substance is impregnated in the biopolymer and the hydrophobic drug is impregnated in a macrophage target ligand, according to an example embodiment.

FIG. 2 is a transmission electron micrograph illustrating the drug carrier according to an example embodiment. More particularly, FIG. 2 is a photograph of a glycol chitosan drug carrier encapsulated with the lobeglitazone.

As the experimental result, the encapsulation efficiency of lobeglitazone in the activated macrophage targetable MAN-PEG-GC-Chol drug carrier had high drug encapsulation efficiency of 95.72±3.32%. Further, as the result analyzed with the transmission electron microscopy, the drug carrier encapsulated with the lobeglitazone had a spherical particle having a size of about 50 to 200 nm.

Experimental Example 2: Drug Release of Drug Carrier Encapsulated with Lobeglitazone A drug release experiment of the drug carrier encapsulated with the lobeglitazone prepared in Example 1 was performed in a PBS solution at pH 7.4. An analysis of the amount of the released drug was performed the same high performance liquid chromatography condition in the Experimental Example 1.

Figure 3:
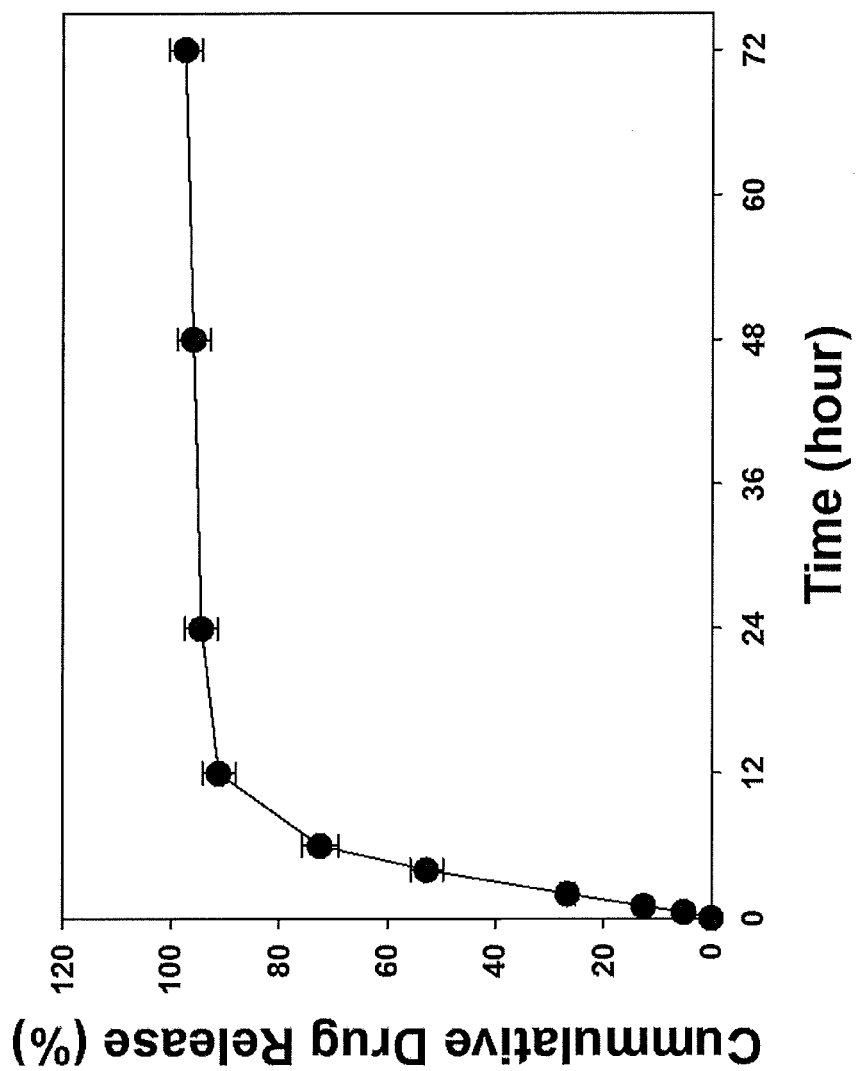
FIG. 3 is a graph illustrating a degree that the drug is released over time from the drug carrier according to an example embodiment.

FIG. 3 is a graph illustrating a degree that the drug is released over time from the drug carrier according to an example embodiment.

Referring to FIG. 3, about 90% of lobeglitazone as the hydrophobic drug from the drug carrier was released within 12 hours and as the experimental result, it is indicated that the drug bound to the drug carrier may be smoothly released in vivo.

Experimental Example 3: Anti-Inflammatory Effect of Drug Carrier Encapsulated with Lobeglitazone In Vitro An anti-inflammatory effect of the drug carrier encapsulated with the lobeglitazone was evaluated by analyzing a quantity of inflammatory cytokines secreted from the activated macrophage. $1 \times 10^6$ of RAW264.7 cells were evenly divided in each 100 Pi dish, treated with the drug carrier encapsulated with the lobeglitazone for 6 hours at a concentration of 0 μM, 10 μM, and 50 μM, and then treated with lipopolysaccharide (LPS) causing inflammation for 3 hours at a concentration of 100 μg/ml to activate the macrophage and then concentrations of TNF-α, IL-6, and MMP-9 as inflammatory factors were measured by using an ELISA kit. The concentrations of TNF-α and IL-6 as the inflammatory cytokines were measured in a supernatant of a cell culture medium and MMP-9 as a protease decomposed the cells and then the concentration of the MMP-9 in the cells was measured.

Figure 4:
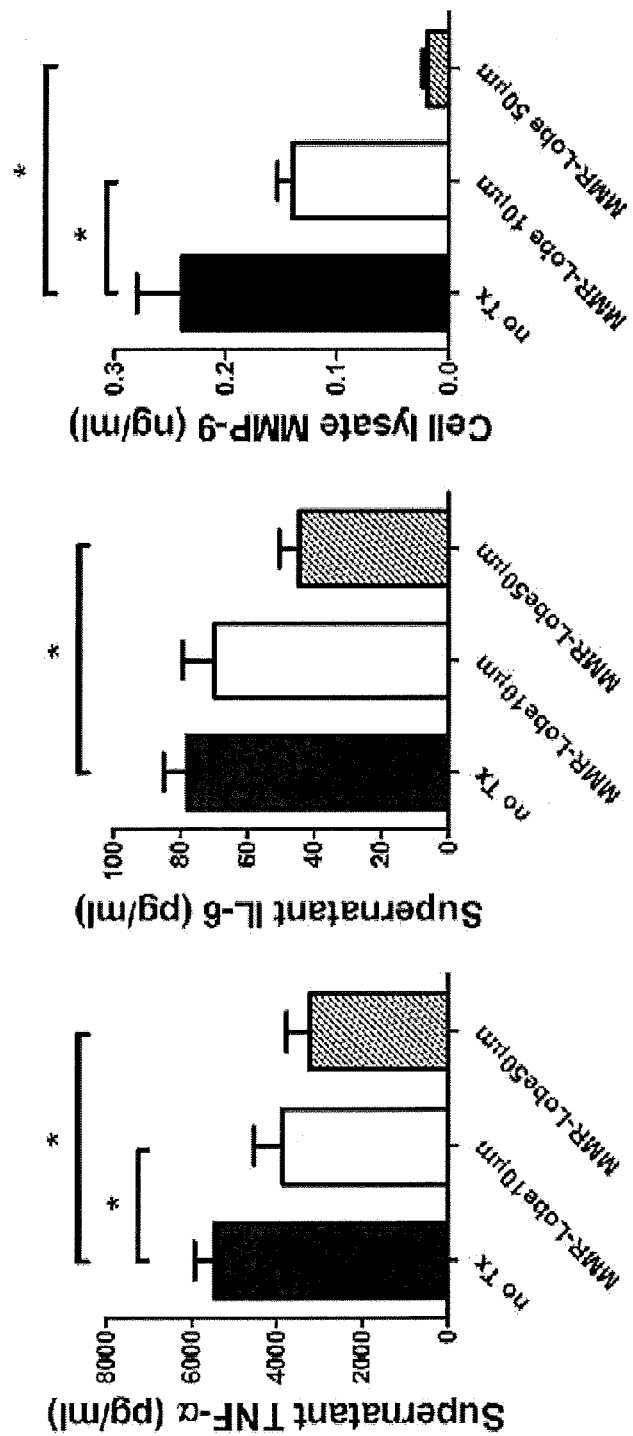
FIG. 4 is a graph illustrating an anti-inflammatory effect of the drug carrier according to an example embodiment.

FIG. 4 is a graph illustrating an anti-inflammatory effect of the drug carrier according to an example embodiment. More particularly, FIG. 4 illustrates the concentrations of TNF-α and IL-6 as the inflammatory factors and MMP-9 as the protease when the glycol chitosan drug carrier encapsulated with the lobeglitazone and the lobeglitazone are treated to the macrophage, respectively and then the lipopolysaccharide (LPS) is additionally treated.

Referring to FIG. 4, in a group treated with the drug carrier encapsulated with the lobeglitazone, it can be verified that amounts of the TNF-α, IL-6, and MMP-9 are significantly reduced according to a treatment concentration of the drug and it is shown that the anti-inflammatory effect is excellent.

Experimental Example 4: Evaluation of Treatment Effect by Imaging Atherosclerosis In Vivo of Drug Carrier Encapsulated with Lobeglitazone In order to evaluate a possibility of reducing inflammation and a size of the atherosclerotic plaque in vivo of the drug carrier encapsulated with the lobeglitazone, the drug carrier encapsulated with the lobeglitazone was administrated in mice (ApoE−/− mice) causing the atherosclerosis at a carotid branch.

More particularly, the ApoE −/− mice with the atherosclerosis are divided into three groups, and then in the first group, a drug carrier encapsulated with a mannose receptor-specific lobeglitazone was administrated (14 mg/kg/week), in the second group, the same quantity of lobeglitazone was orally administrated (14 mg/kg/week), and in the third group, a treating drug was not administrated. After the drug was administrated for four weeks, the same carotid branch portion was peeled and the size and the inflammation degree of the atherosclerotic plaque before and after treatment were observed and compared by a general microscope and an in-vivo fluorescence microscope.

Particularly, the effect of treating atherosclerosis was evaluated by comparing and analyzing an atherosclerotic size and an inflammation degree before administrating the drug and after administrating the drug for four weeks by administrating a glycol chitosan-based drug carrier (attached with a fluorescent material) capable of imaging an atherosclerotic plaque selectively bound to the mannose receptor over-expressed in the macrophage to an atherosclerotic model mouse and then peeling the carotid branch portion to image the carotid branch portion by an in-vivo fluorescence microscope.

Figure 5A:
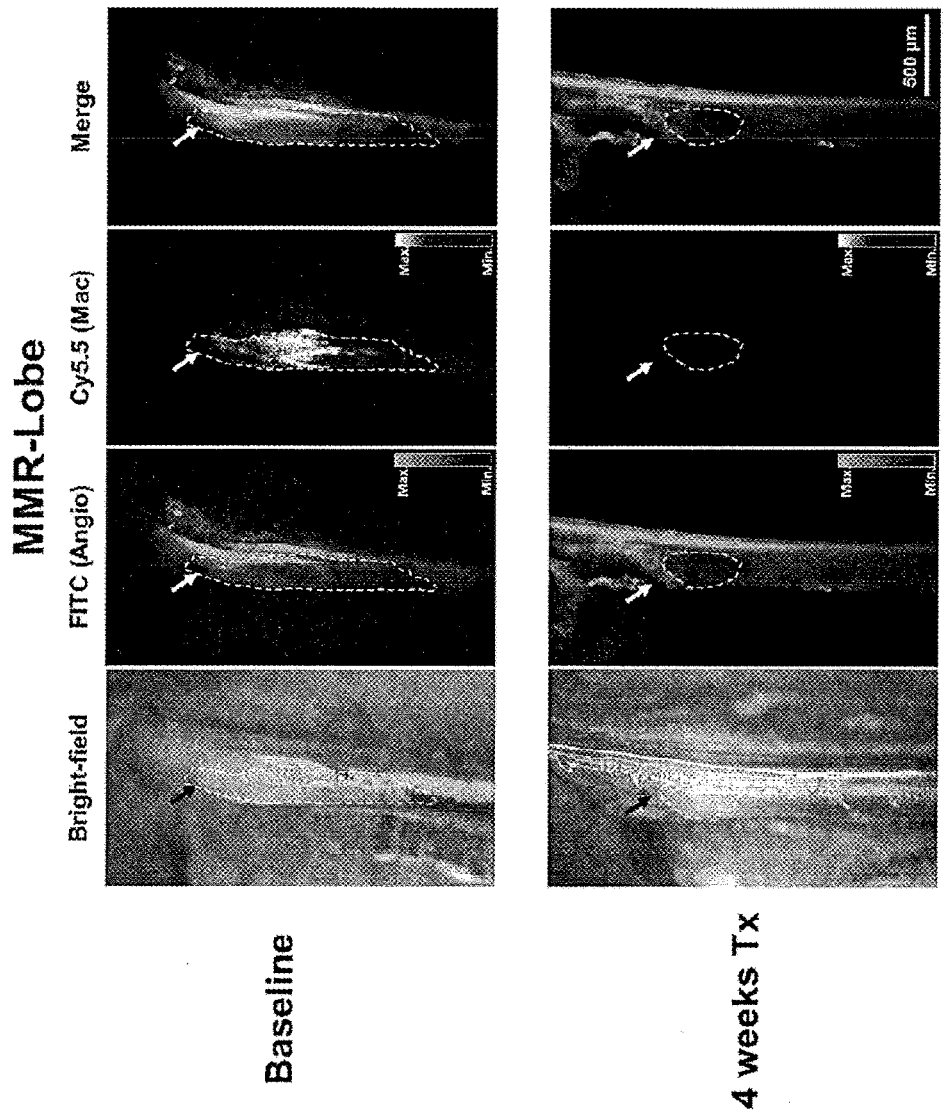
FIGS. 5A, 5B and 5C are photographs illustrating sizes of atherosclerotic plaques and sizes of inflammation in a group administered with the drug carrier according to an example embodiment, a group administered orally with lobeglitazone, and a group administered with no drug.
Figure 5B:
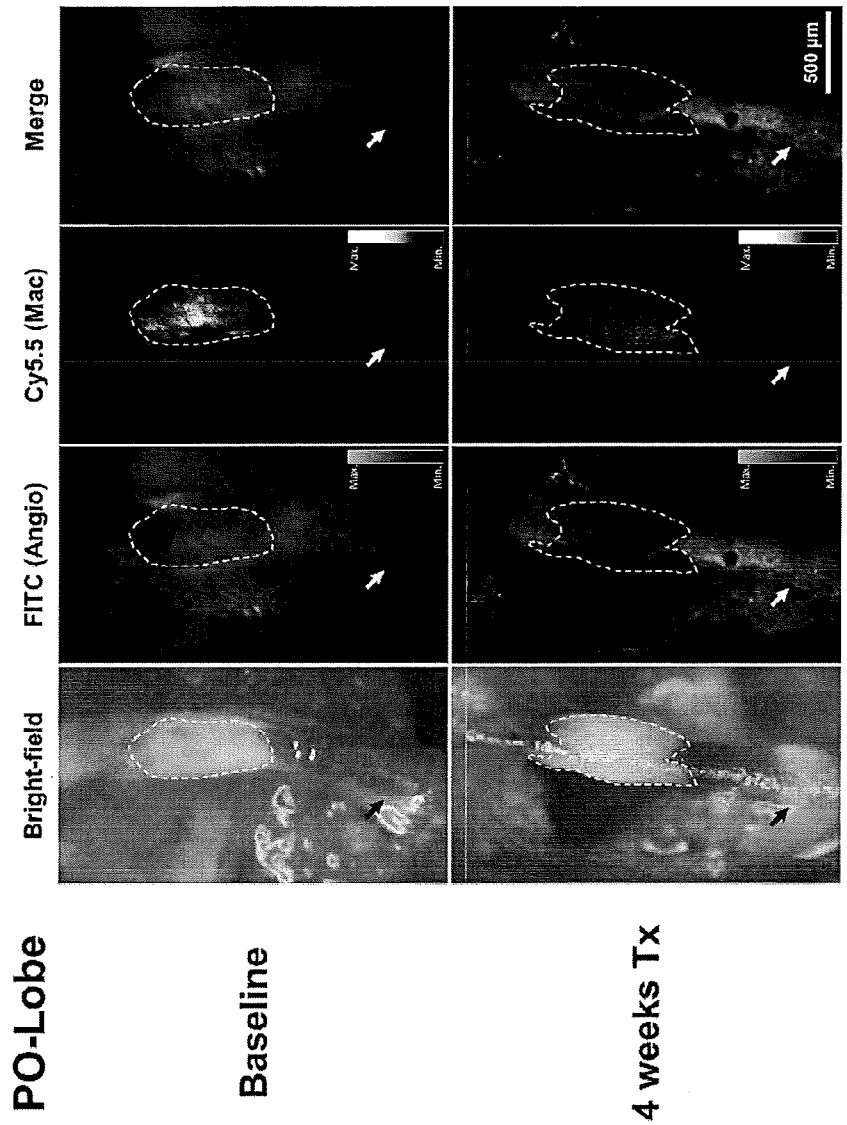
Figure 5C:
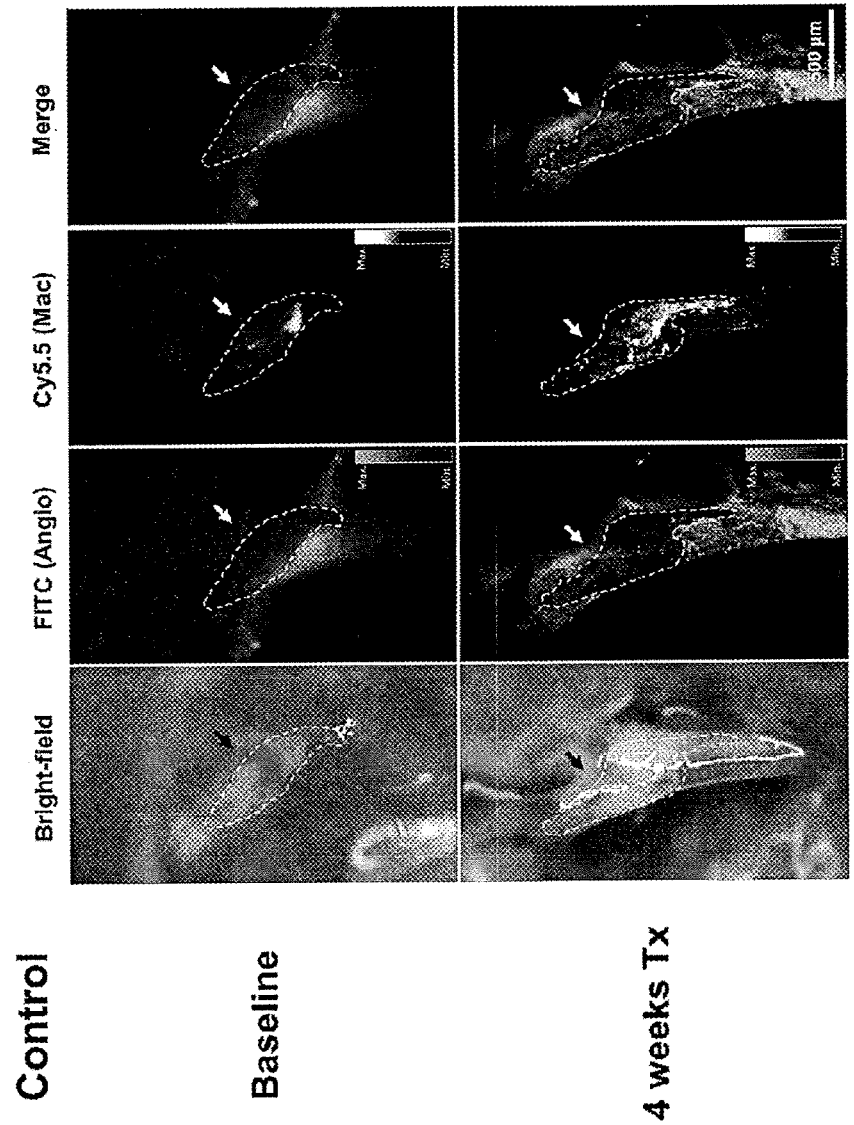

FIGS. 5A, 5B and 5C are photographs illustrating sizes of atherosclerotic plaques and sizes of inflammation, respectively in a group administered with the drug carrier according to an example embodiment, a group administered orally with lobeglitazone, and a group administered with no drug. FIGS. 5A to 5C are fluorescent image photographs capable of verifying the size and the inflammation of the atherosclerotic plaque in the carotid before administrating the drug and after administrating the drug for four weeks, respectively, in a group (MMR-lobe) administrated with a glycol chitosan drug carrier encapsulated with lobeglitazone, a group (PO-Lobe) orally administrated with lobeglitazone, and a group (Control) administrated with no drug, respectively.

Referring to FIGS. 5A to 5C, in the group administrated with the drug carrier encapsulated with the lobeglitazone, the size and the inflammation degree of the atherosclerosis were significantly reduced, in the group administrated with the lobeglitazone as an oral treating agent, the size and the inflammation degree of the atherosclerosis were not largely changed, and in the group administrated with no drug, the size and the inflammation degree of the atherosclerosis were significantly increased.

In order to objectively quantify the inflammation degree expressed in the atherosclerotic plaque, a signal of autofluorescence or more of the atherosclerotic plaque measured in the Experimental Example 4 was extracted to quantify the range of signal expression and the degree of signal intensity.

Figure 6:
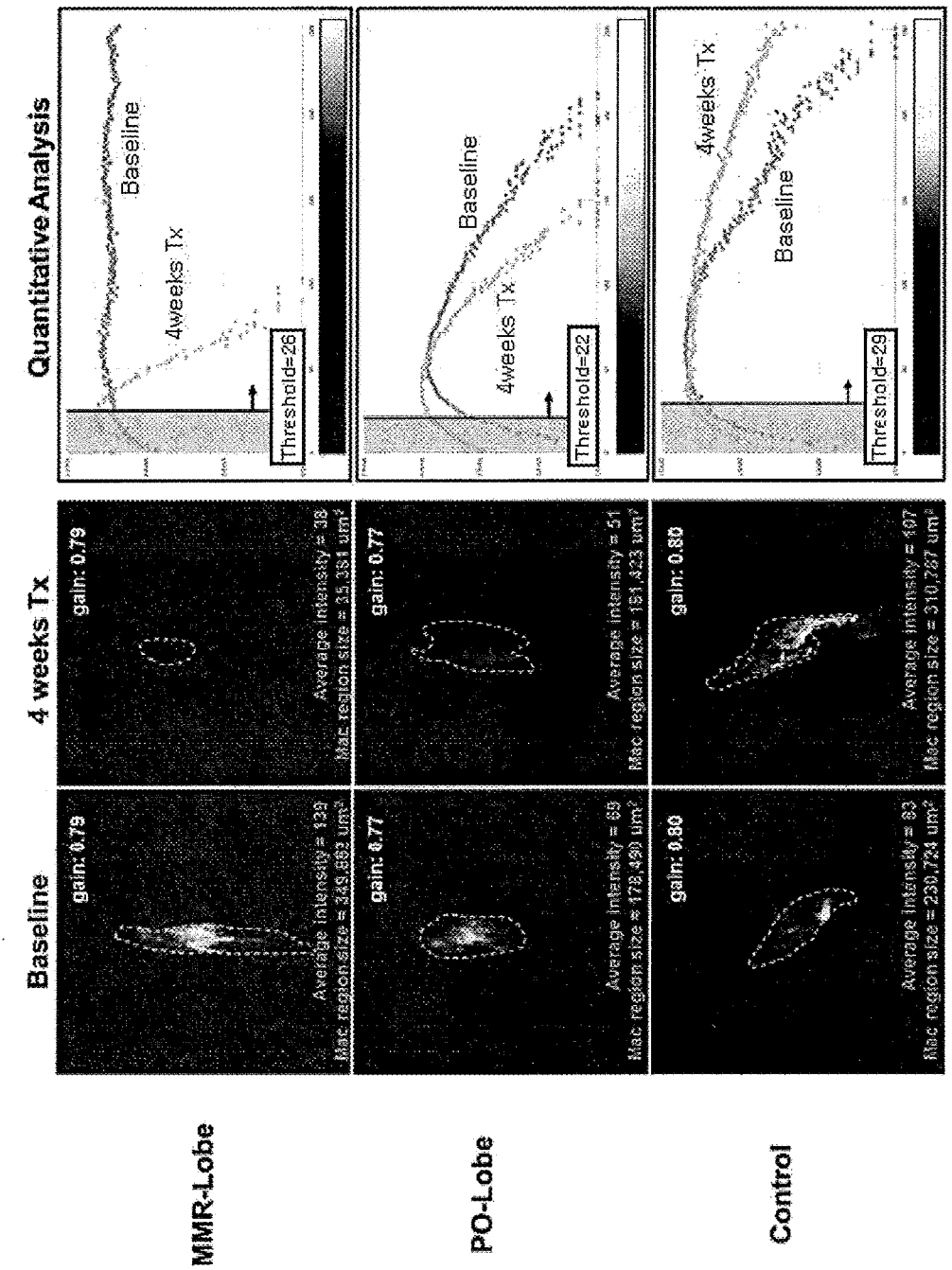
FIG. 6 is a graph of quantifying a fluorescence signal expressed in atherosclerotic plaques in the group administered with the drug carrier according to an example embodiment, the group administered orally with lobeglitazone, and the group administered with no drug.

FIG. 6 is a graph of quantifying fluorescence signals expressed in atherosclerotic plaques in the group administered with the drug carrier according to an example embodiment, the group administered orally with lobeglitazone, and the group administered with no drug. FIG. 6 is a graph of quantitatively comparing fluorescence intensities expressed in the atherosclerotic plaque in the carotid before administrating the drug and after administrating the drug for four weeks, respectively, in a group (MMR-lobe) administrated with a glycol chitosan drug carrier encapsulated with lobeglitazone, a group (PO-Lobe) orally administrated with lobeglitazone, and a group (Control) administrated with no drug, respectively.

Referring to FIG. 6, in the group administrated with the drug carrier encapsulated with the lobeglitazone, the fluorescence intensity was significantly decreased, whereas in the group administrated with the lobeglitazone as an oral treating agent, there was no difference in the fluorescence intensity, and in the group administered with no drug, the fluorescence intensity was increased.

Figure 7:
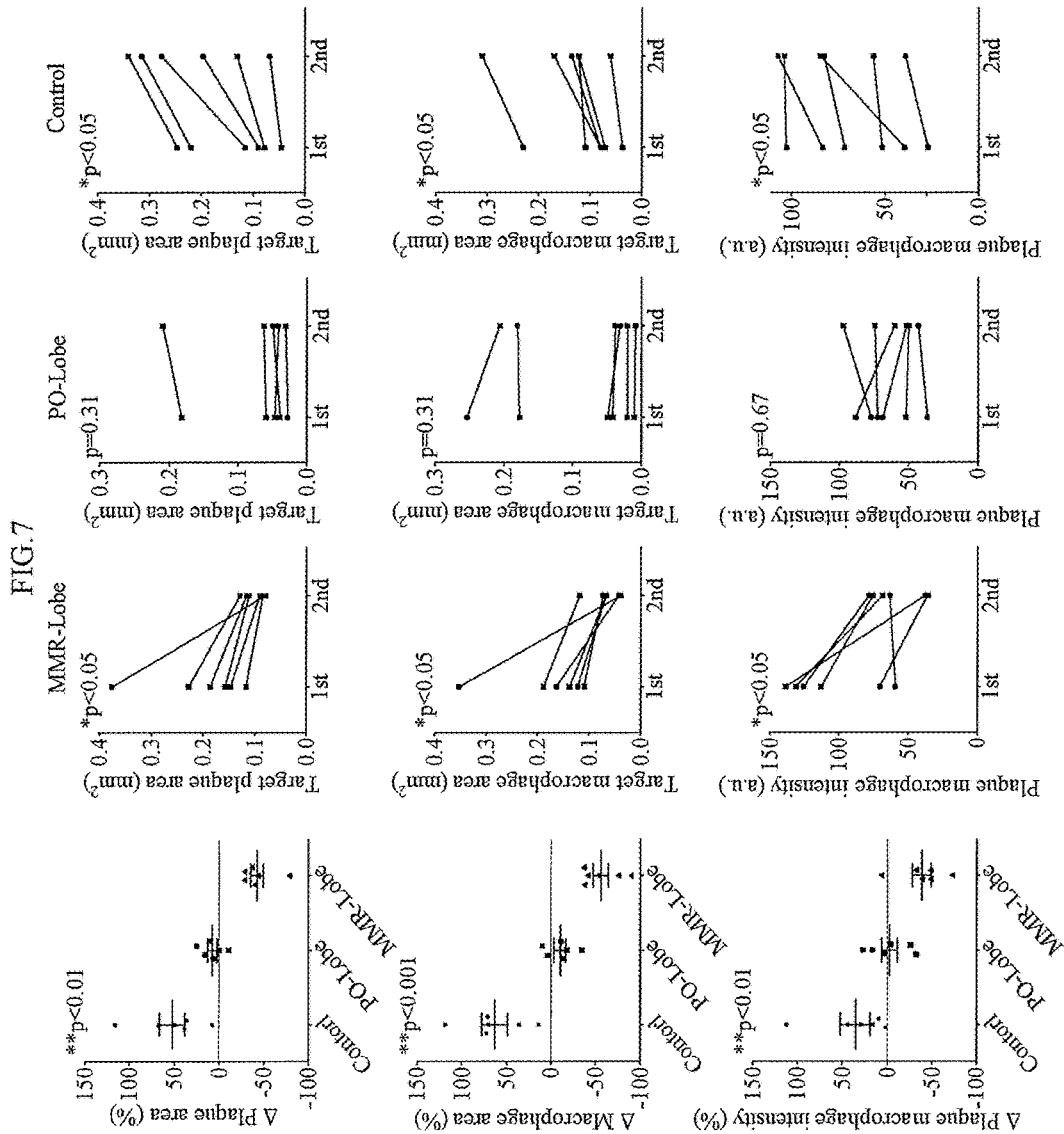
FIG. 7 is a graph of converting and comparing sizes of atherosclerotic plaques and sizes of inflammation to quantitative values in the group administered with the drug carrier according to an example embodiment, the group administered orally with lobeglitazone, and the group administered with no drug.

FIG. 7 is a graph of converting and comparing sizes of atherosclerotic plaques and sizes of inflammation to quantitative values in the group administered with the drug carrier according to an example embodiment, the group administered orally with lobeglitazone, and the group administered with no drug. FIG. 7 is a graph of quantitatively comparing a size change and an inflammation reduction degree of the atherosclerotic plaque in an individual animal for each group with an average value for the size change and the inflammation reduction degree of the atherosclerotic plaque in the carotid before administrating the drug and after administrating the drug for four weeks, respectively, in a group (MMR-lobe) administrated with a glycol chitosan drug carrier encapsulated with lobeglitazone, a group (PO-Lobe) orally administrated with lobeglitazone, and a group (Control) administrated with no drug, respectively.

Referring to FIG. 7, the size of the atherosclerotic plaque, the inflammation range, and the inflammation degree may be verified in many objects for each group, an particularly, in the group (MMR-lobe) administrated with the glycol chitosan drug carrier encapsulated with lobeglitazone, it can be verified that the size of the atherosclerotic plaque, the inflammation range, and the inflammation degree are significantly decreased.

Experimental Example 5: Evaluation of Effect of Treating Atherosclerosis In Vitro and Histopathology Analysis of Drug Carrier Encapsulated with Lobeglitazone After evaluating the effect of treating atherosclerosis at the carotid branch portion by an imaging experiment in vivo, a mouse was euthanized and the aorta was peeled (en face), and then the inflammation degree of the atherosclerotic plaque and the range of the atherosclerotic plaque in the blood were evaluated by in-vitro fluorescence imaging and Oil red O staining.

Figure 8:
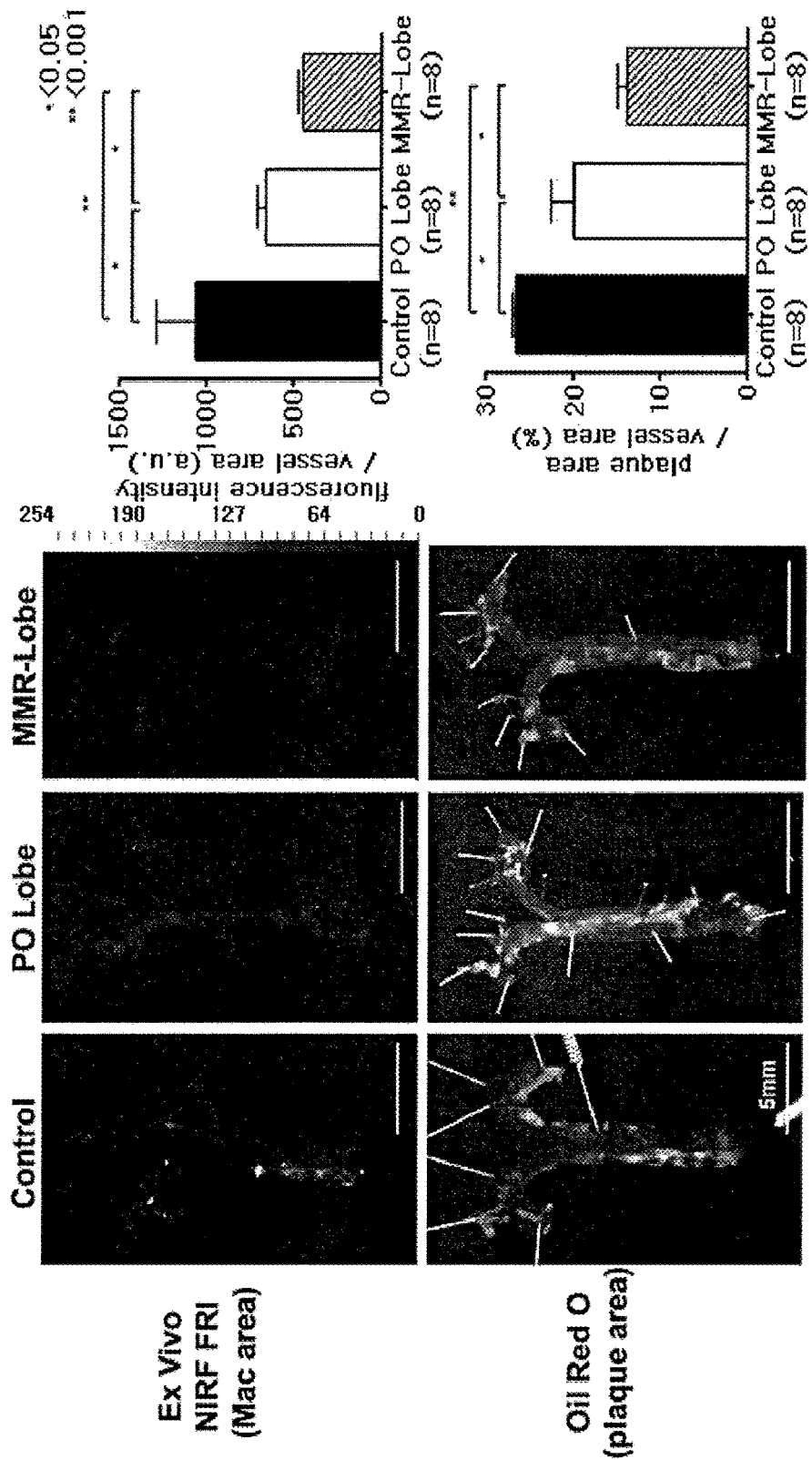
FIG. 8 is a graph illustrating a fluorescence photograph and fluorescence intensity representing sizes of atherosclerotic plaques by using in-vitro fluorescence imaging and Oil red O staining in the group administered with the drug carrier according to an example embodiment, the group administered orally with lobeglitazone, and the group administered with no drug.

FIG. 8 is a graph illustrating a fluorescence photograph and fluorescence intensity representing sizes of atherosclerotic plaques by using in-vitro fluorescence imaging and Oil red O staining in the group administered with the drug carrier according to an example embodiment, the group administered orally with lobeglitazone, and the group administered with no drug. FIG. 8 illustrates a fluorescence intensity and an Oil Red O staining photograph in the atherosclerotic blood vessel before administrating the drug and after administrating the drug for four weeks, respectively, in a group (MMR-lobe) administrated with a glycol chitosan drug carrier encapsulated with lobeglitazone, a group (PO-Lobe) orally administrated with lobeglitazone, and a group (Control) administrated with no drug, respectively, and illustrates a graph of quantitatively comparing a fluorescence intensity and a size of the atherosclerotic plaque in the atherosclerotic blood vessel.

Referring to FIG. 8, in the group (MMR-lobe) administrated with the glycol chitosan drug carrier encapsulated with lobeglitazone, it can be verified that the inflammation degree and the inflammation range of the atherosclerotic plaque in the blood vessel are significantly low.

Further, the effect of treating atherosclerosis of the drug carrier encapsulated with the lobeglitazone was evaluated by histopathologically analyzing the size of the atherosclerotic plaque reflecting the inflammation degree of the atherosclerotic plaque, distribution of the macrophages, and expression of mannose receptors in the macrophage. The atherosclerotic plaque of the carotid extracted from the arteriosclerosis model mouse was stained by H&E staining, MAC3 staining (macrophage staining), and CD 206 staining (macrophage mannose receptor staining).

Figure 9:
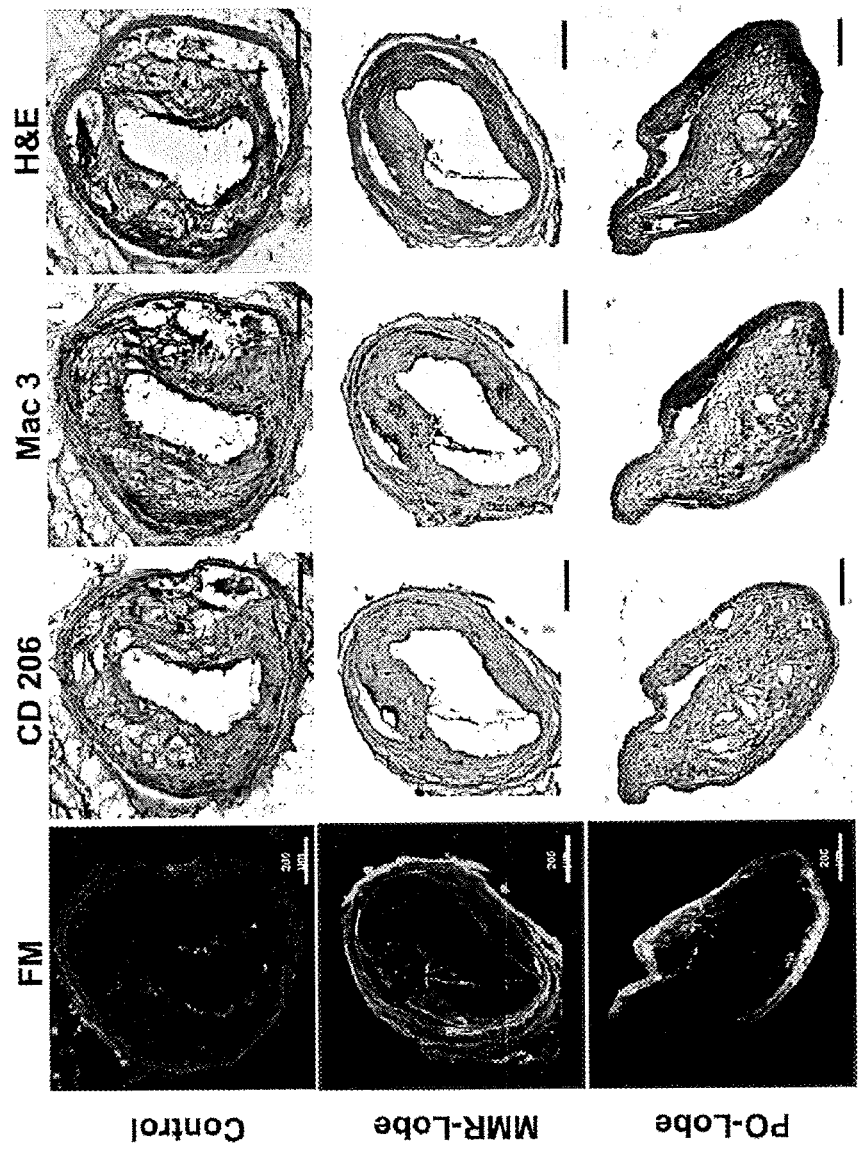
FIG. 9 is a photograph illustrating sizes of atherosclerotic plaques by using H&E staining, MAC3 staining, and CD 206 staining in the group administered with the drug carrier according to an example embodiment, the group administered orally with lobeglitazone, and the group administered with no drug.

FIG. 9 is a photograph illustrating sizes of atherosclerotic plaques by using H&E staining, MAC3 staining, and CD 206 staining in the group administered with the drug carrier according to an example embodiment, the group administered orally with lobeglitazone, and the group administered with no drug. FIG. 9 is a photograph illustrating an atherosclerotic plaque in the carotid extracted from the mouse by CD 206 staining (macrophage mannose receptor staining), MAC3 staining (macrophage staining), and H&E staining, before administrating the drug and after administrating the drug for four weeks, respectively, in a group (MMR-lobe) administrated with a glycol chitosan drug carrier encapsulated with lobeglitazone, a group (PO-Lobe) orally administrated with lobeglitazone, and a group (Control) administered with no drug, respectively.

Referring to FIG. 9, in the group administered with no drug, the formation of the atherosclerotic plaque and the MAC3 and the CD 206 were strongly expressed, and it is meant that macrophage infiltration is active. However, in the group (MMR-lobe) administrated with a glycol chitosan drug carrier encapsulated with lobeglitazone and the group (PO-Lobe) orally administrated with lobeglitazone, the size of the atherosclerotic plaque, MAC3, and CD 206 were decreased, and particularly, in the group (MMR-lobe) administrated with a glycol chitosan drug carrier encapsulated with lobeglitazone, it was verified that the size of the atherosclerotic plaque, MAC3, and CD 206 were more significantly decreased.

Figure 24:
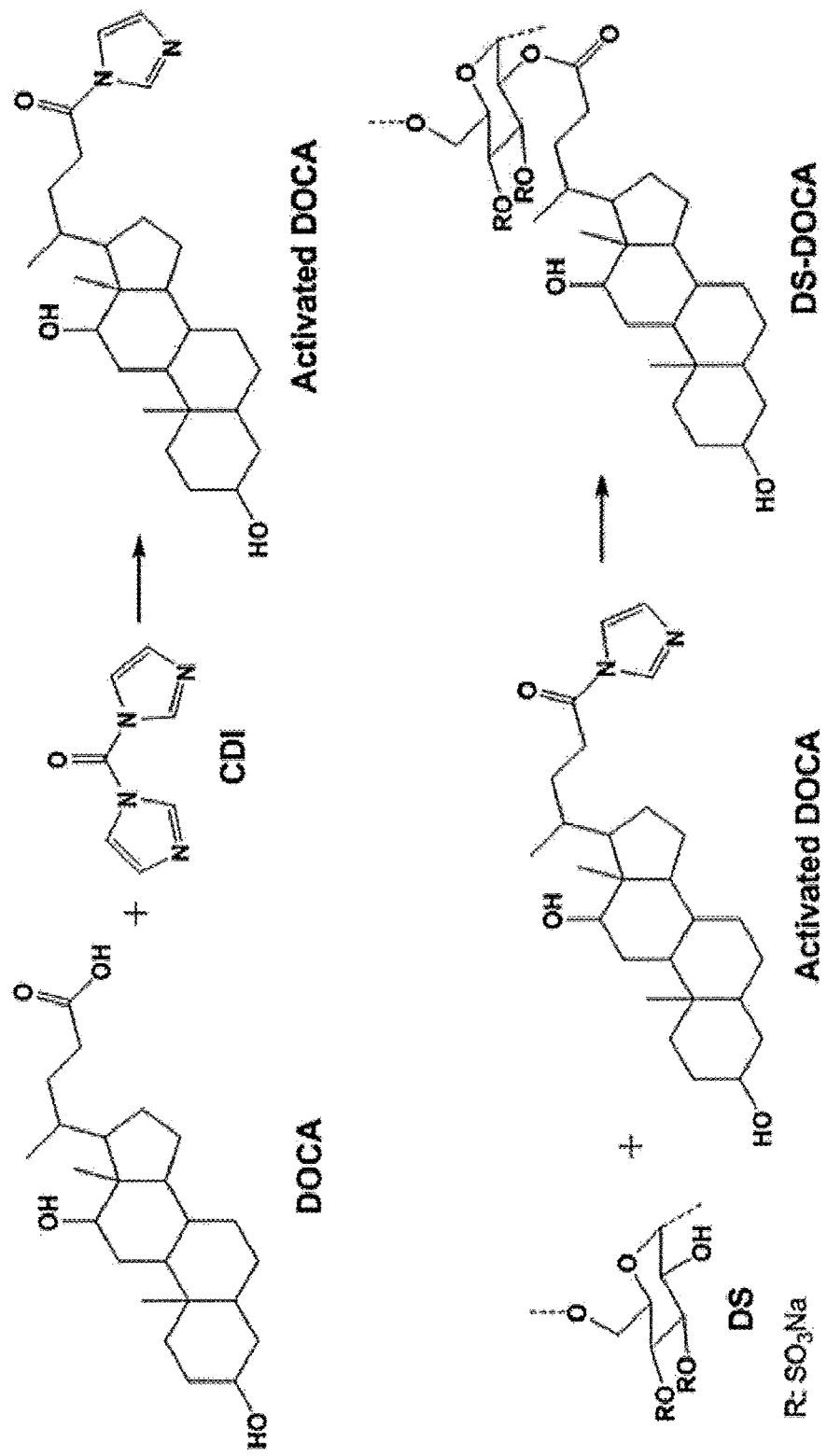
FIG. 24 illustrates a Reaction Formula 3.

Experimental Example 6: Synthesis of Amphipathic Polymer Targetable to Activated Macrophage and Preparation of Nanoparticles 400 mg of deoxycholic acid well-dried in a vacuum state and N,N'-carbonyldiimidazole (CDI) as a crosslinker were put in 50 ml of a round flask, dissolved in 20 ml of a tetrahydrofuran solvent, and then reacted for 6 hours at 70° C. to remove the solvent by a rotary evaporator. The activated deoxycholic acid and 500 mg of dextran sulfate were dissolved in 30 ml of dimethyl sulfoxide and then reacted for 48 hours at 90° C. In order to remove the non-reacted deoxycholic acid and the crosslinker, the activated deoxycholic acid was dialyzed in distilled water for 2 days and filtered, and then lyophilized. 1 mg of the lyophilized dextran sulfate-deoxycholic acid amphiphilic polymer was dispersed in distilled water and then the nanoparticles were prepared, and the shape and the size of the particle were analyzed by a transmission electron microscope. These prepared processes are shown in FIG. 24 illustrating a Reaction Formula 3.

Figure 10:
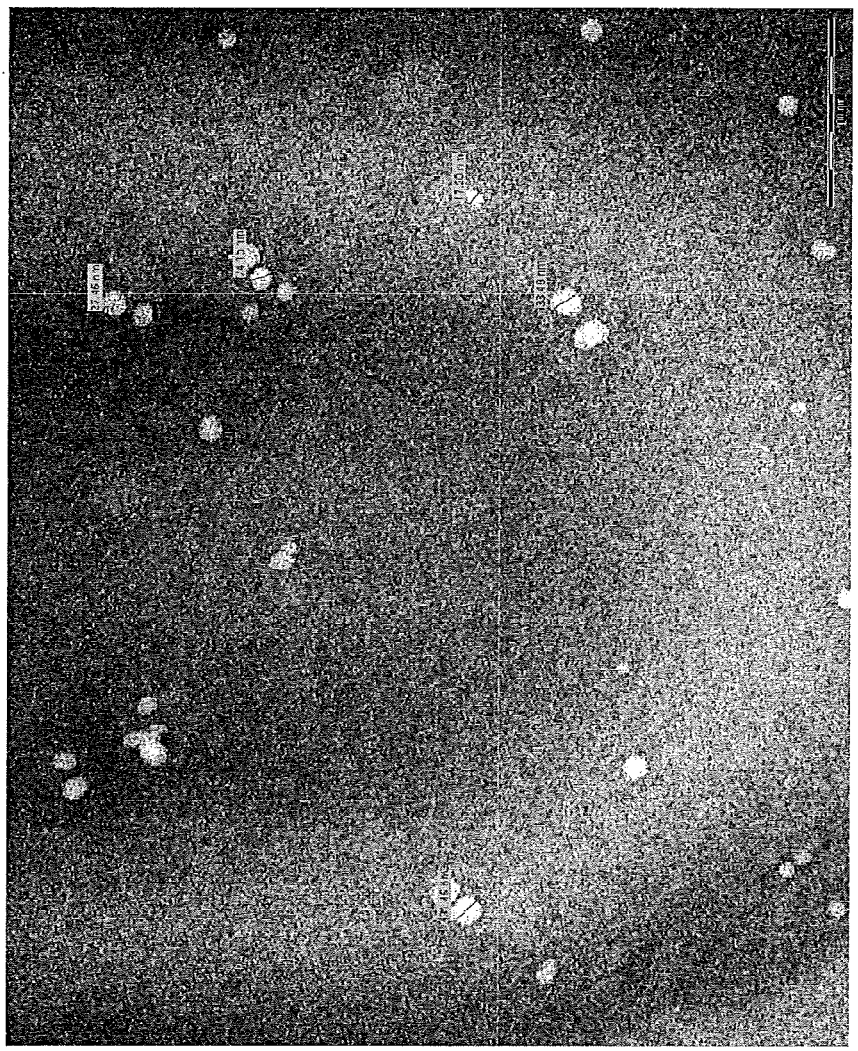
FIG. 10 is a transmission electron micrograph of nanoparticles prepared by binding the hydrophobic substance to the ligand polymer which is selectively bound to the macrophage, according to an example embodiment.

Referring to FIG. 10, the nanoparticle prepared by the dextran sulfate-deoxycholic acid had a spherical particle shape having a size of 17 to 34 nm.

Experimental Example 7: Preparation of Nanoparticle Constituted by Activated Macrophage Targetable Amphipathic Polymer and Hydrophobic Synthetic Polymer and Drug Carrier Encapsulated with Lobeglitazone The nanoparticles constituted by an activated macrophage targetable amphipathic polymer and a hydrophobic synthetic polymer were prepared by a dialyzing method and a sonicating method. In the dialyzing method, 20 mg of dextran sulfate-deoxycholic acid and 80 mg of a polylactic-co-glycolic acid polymer were dissolved in 10 ml of dimethyl sulfoxide, dialyzed in distilled water for 2 days, centrifuged, and then lyophilized. In the sonicating method, 20 mg of dextran sulfate-deoxycholic acid was dissolved in 1.5 ml of distilled water, 80 mg of the polylactic-co-glycolic acid polymer was dissolved in 1 ml of dichloromethane, and then the two solutions were mixed with each other, treated with a probe type ultrasound to prepare an emulsion, and dispersed in 40 ml of distilled water, stirred for 2 hours at 40° C. to remove an organic solvent, centrifuged, and then lyophilized. In a method of preparing the drug carrier encapsulated with the lobeglitazone, 30 mg of lobeglitazone was dissolved in 200 µl of methanol, put in 80 mg of the polylactic-co-glycolic acid polymer dissolved in 1 ml of dichloromethane, and then mixed with each other. The organic solvent dissolved with the drug and the polymer was mixed with 20 mg of dextran sulfate-deoxycholic acid dissolved in 1.5 ml of distilled water and then treated with a probe type ultrasound to prepare an emulsion, and then dispersed in 40 ml of distilled water and stirred for 2 hours at 40° C. to remove the organic solvent, centrifuged, and then lyophilized. The shapes and the sizes of the lyophilized nanoparticles were analyzed by a scanning electron microscope.

Figure 11:
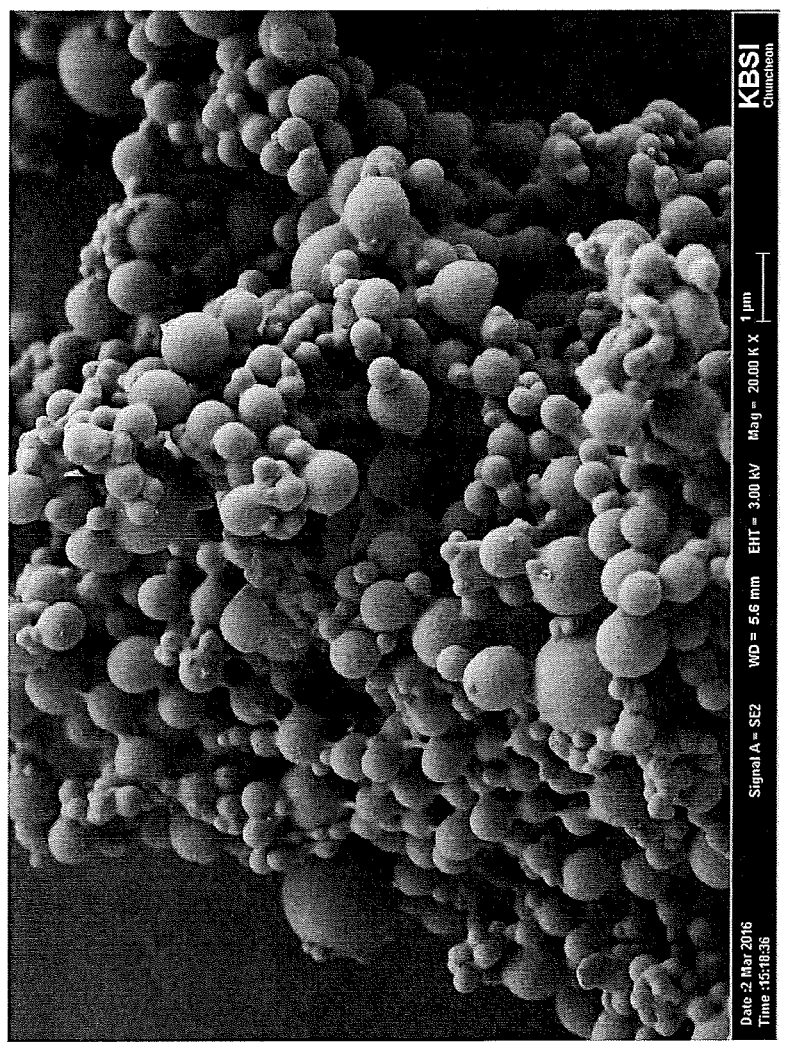
FIG. 11 is a scanning electron micrograph of nanoparticles prepared by a method of dialyzing an amphipathic polymer in which the hydrophobic substance is bound to the ligand polymer which is selectively bound to the macrophage and a hydrophobic synthetic polymer, according to an example embodiment.

FIG. 11 is a scanning electron micrograph of nanoparticles prepared by a method of dialyzing the amphipathic polymer in which the hydrophobic substance is bound to the ligand polymer which is selectively bound to the macrophage and the hydrophobic synthetic polymer, according to an example embodiment.

Figure 12:
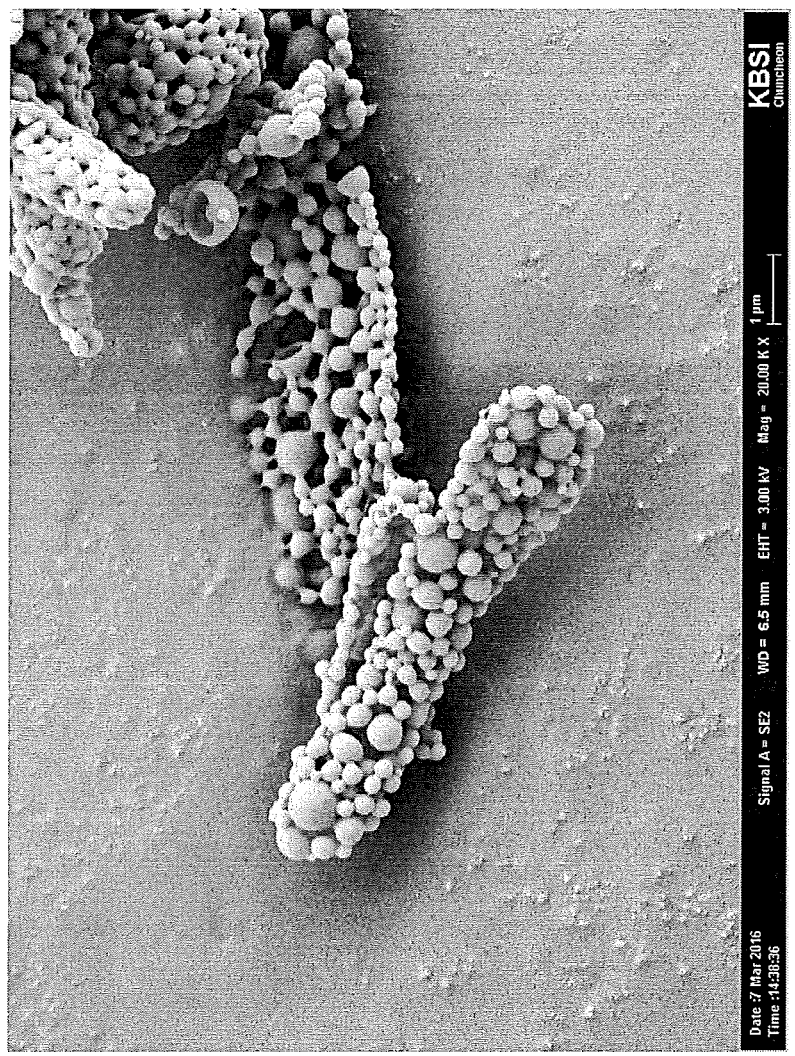
FIG. 12 is a scanning electron micrograph of nanoparticles prepared by a method of sonicating the amphipathic polymer in which the hydrophobic substance is bound to the ligand polymer which is selectively bound to the macrophage and the hydrophobic synthetic polymer, according to an example embodiment.

FIG. 12 is a scanning electron micrograph of nanoparticles prepared by a method of sonicating the amphipathic polymer in which the hydrophobic substance is bound to the ligand polymer which is selectively bound to the macrophage and the hydrophobic synthetic polymer, according to an example embodiment.

Figure 13:
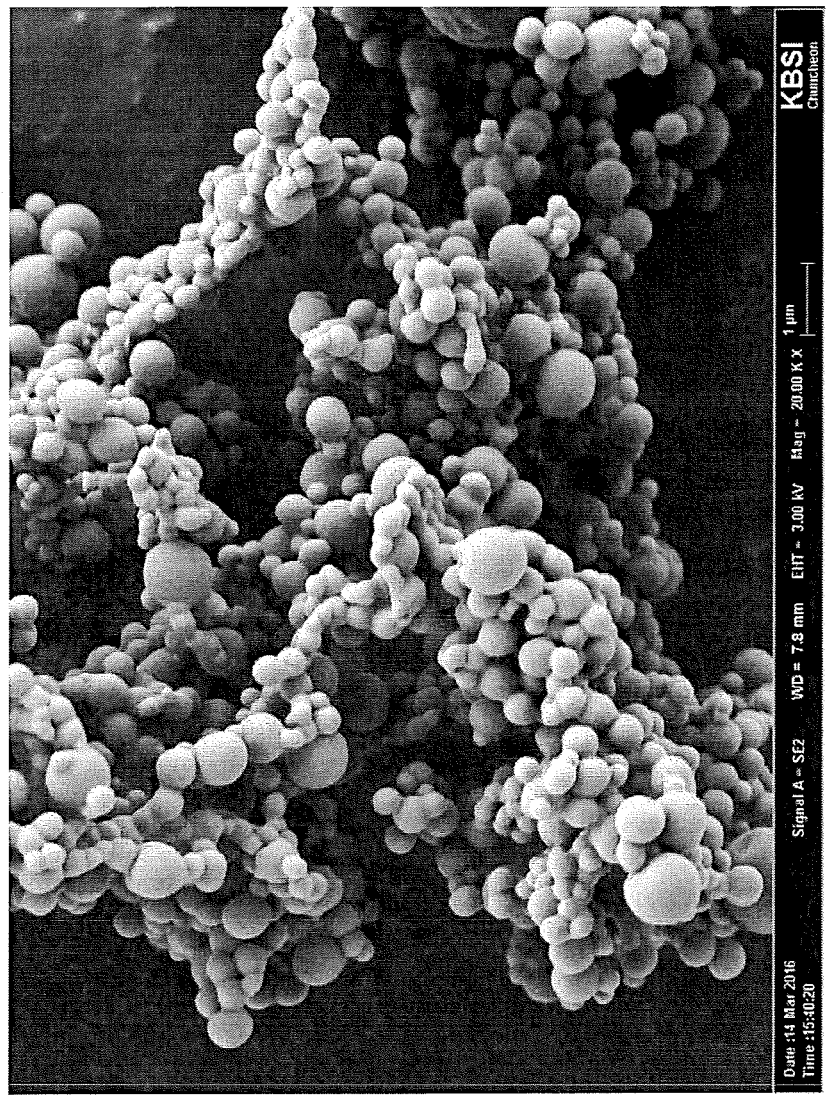
FIG. 13 is a scanning electron micrograph of a drug carrier including nanoparticles prepared by a method of sonicating the amphipathic polymer and the hydrophobic synthetic polymer and lobeglitazone according to an example embodiment.

FIG. 13 is a scanning electron micrograph of a drug carrier including nanoparticles prepared by a method of sonicating the amphipathic polymer and the hydrophobic synthetic polymer and lobeglitazone according to an example embodiment.

Referring to FIG. 11, the nanoparticle prepared by a dialyzing method had a spherical particle shape having a size of 50 nm to 1,000 nm.

Referring to FIG. 12, the nanoparticle prepared by a sonicating method had a spherical particle shape having a size of 100 nm to 500 nm.

Referring to FIG. 13, the nanoparticle encapsulated with lobeglitazone prepared by a sonicating method had a spherical particle shape having a size of 100 nm to 500 nm.

According to example embodiments, the drug carrier may include an amphipathic polymer including a macrophage ligand polymer or a target ligand recognizing the macrophage, and a hydrophobic drug, to selectively target a receptor expressed in activated macrophages in atherosclerotic plaques, thereby delivering a drug at a high concentration. It is possible to suppress the spread of atherosclerotic diseases at all stages of development, progression and rupture of atherosclerosis or to prevent various complications due to atherosclerosis by using the drug carrier.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A drug carrier for treatment of atherosclerosis, the drug carrier consisting of:
   an amphipathic polymer consisting of a hydrophilic polymer, a hydrophobic substance, and a target ligand recognizing a mannose receptor of a macrophage; and
   a hydrophobic drug for treatment of atherosclerosis,
   wherein the hydrophilic polymer is a chitosan derivative, and
   the hydrophobic substance is a cholesterol derivative.

2. The drug carrier of claim 1, wherein the target ligand recognizing the mannose receptor of the macrophage includes: mannose amine or mannose phosphate.

3. The drug carrier of claim 1, wherein the hydrophobic drug for treatment of atherosclerosis includes at least one selected from the group consisting of statin drugs, PPAR-gamma agonist drugs, DPP-4 inhibitor drugs, angiotensin converting enzyme inhibitor drugs, angiotensin II receptor blockers, PCSK9 inhibitors, and antioxidants.

4. A method of preparing the drug carrier of claim 1 for treatment of atherosclerosis, the method comprising preparing the amphipathic polymer; forming nanoparticles by self-assembling the amphipathic polymer and impregnating the hydrophobic drug in the nanoparticles.

5. A drug carrier for treatment of atherosclerosis, the drug carrier consisting of:
   a first amphipathic polymer including a macrophage ligand polymer and a hydrophobic substance;
   a second amphipathic polymer consisting of a hydrophilic polymer, said hydrophobic substance, and a target ligand recognizing a mannose receptor of a macrophage; and
   a hydrophobic drug for treatment of atherosclerosis,
   wherein the macrophage ligand polymer is a dextran derivative,
   the hydrophobic substance is a cholesterol derivative, and
   the hydrophilic polymer is a chitosan derivative.

6. A method for preparing the drug carrier of claim 5, the method comprising: preparing the first amphipathic polymer; preparing the second amphipathic polymer; forming nanoparticles by self-assembling the amphipathic polymers; and impregnating the hydrophobic drug in the nanoparticles.

7. A drug carrier for treatment of atherosclerosis, the drug carrier consisting of:
   a first amphipathic polymer including a macrophage ligand polymer, a hydrophobic substance, and a target ligand recognizing a mannose receptor of a macrophage;
   a second amphipathic polymer consisting of a hydrophilic polymer, a hydrophobic substance, and a target ligand recognizing a mannose receptor of a macrophage; and
   a hydrophobic drug for treatment of atherosclerosis,
   wherein the macrophage ligand polymer is a dextran derivative,
   the hydrophobic substance is a cholesterol derivative, and
   the hydrophilic polymer is a chitosan derivative.

* * * * *